United States Patent
Herranz et al.

(10) Patent No.: US 9,636,366 B2
(45) Date of Patent: May 2, 2017

(54) BACTEROIDES CECT 7771 AND THE USE THEREOF IN THE PREVENTION AND TREATMENT OF EXCESS WEIGHT, OBESITY AND METABOLIC AND IMMUNOLOGICAL ALTERATIONS

(71) Applicant: Consejo Superior de Investigaciones Científicas, Madrid (ES)

(72) Inventors: Yolanda Sanz Herranz, Valencia (ES); Paola Gauffin Cano, Valencia (ES); Yolanda Arlette Santacruz, Valencia (ES); Ángela Moya Pérez, Valencia (ES); Moisés Laparra Llopis, Valencia (ES)

(73) Assignee: Consejo Superior de Investigaciones Científicas, Madrid (ES)

( * ) Notice: Subject to any disclaimer, the term of this patent is extended or adjusted under 35 U.S.C. 154(b) by 0 days.

(21) Appl. No.: 14/403,930

(22) PCT Filed: May 16, 2013

(86) PCT No.: PCT/ES2013/070309
§ 371 (c)(1),
(2) Date: Apr. 10, 2015

(87) PCT Pub. No.: WO2013/175038
PCT Pub. Date: Nov. 28, 2013

(65) Prior Publication Data
US 2015/0216913 A1   Aug. 6, 2015

(30) Foreign Application Priority Data

May 25, 2012   (ES) .................................. 201230796

(51) Int. Cl.
| | | |
|---|---|---|
| A61K 35/74 | (2015.01) | |
| A61K 45/06 | (2006.01) | |
| C12N 1/20 | (2006.01) | |
| C12R 1/01 | (2006.01) | |
| A23C 9/152 | (2006.01) | |
| A61K 35/741 | (2015.01) | |

(52) U.S. Cl.
CPC .............. *A61K 35/74* (2013.01); *A23C 9/152* (2013.01); *A61K 35/741* (2013.01); *A61K 45/06* (2013.01); *C12N 1/20* (2013.01); *C12R 1/01* (2013.01)

(58) Field of Classification Search
CPC ...... A61K 35/74; A61K 35/741; A61K 45/06; A61K 9/00; C12N 1/20
See application file for complete search history.

(56) References Cited

U.S. PATENT DOCUMENTS

2009/0110664 A1   4/2009   Moore

FOREIGN PATENT DOCUMENTS

| CA | 2810698 A1 | 3/2012 |
|---|---|---|
| EP | 2359838 A1 | 8/2011 |
| WO | WO-2008/076696 A2 | 6/2008 |
| WO | WO-2009/055362 A1 | 4/2009 |

OTHER PUBLICATIONS

Renouf et al 2011, J Nutr. 141(6):1120-6.*
Hong et al 2008, Appl. Environ. Microbiol. vol. 74 No. 9 2882-2893.*
Marhoffer et al., "Impairment of Polymorphonuclear Leukocyte Function and Metabolic Control of Diabetes," Diabetes Care, vol. 15, No. 2 (1992).
Musso et al., "A Meta-Analysis of Randomized Trials for the Treatment of Nonalcoholic Fatty Liver Disease," Hepatology, vol. 52, No. 1, pp. 80-104 (2010).
Turnbaugh et al., "An Obesity-Associated Gut Microbiome with Increased Capacity for Energy Harvest," Nature, vol. 444, pp. 1027-1031 (2006).
Cani et al., Interplay between obesity and associated metabolic disorders: new insights into the gut microbiota, Curr. Opin. Pharmacol., 9(6):737-43 (2009).
Chang et al., Decreased cell-mediated immunity in patients with non-insulin-dependent diabetes mellitus, Diabetes Res. Clin. Pract., 28(2):137-46 (1995).
Delahooke et al., Tumor necrosis factor induction by an aqueous phenol-extracted lipopolysaccharide complex from *Bacteroides* species, Infect. Immun., 63(3):840-6 (1995).
Gerozissis, Brain insulin and feeding: a bi-directional communication, Eur. J. Pharmacol., 490(1-3):59-70 (2004).
Griffin Cano et al., Bacteroides uniformis CECT 7771 ameliorates metabolic and immunological dysunction in mice with high-fat-diet induced obesity, PLoS One, 7:1-16 (2012).
International Search Report and Written Opinion (Spanish and English), corresponding International Application No. PCT/ES2013/070309, mailed Oct. 9, 2013.

(Continued)

Primary Examiner — Padma V Baskar
(74) Attorney, Agent, or Firm — Marshall, Gerstein & Borun LLP

(57) ABSTRACT

The invention relates to a strain of *Bacteroides uniformes* with registration number CECT 7771, and to the cellular constituents, metabolites and/or secreted molecules thereof. The invention also relates to a composition (nutritional or pharmaceutical) comprising at least one of the previous products. The invention further relates to the use of a strain of *Bacteroides uniforms*, preferably CECT 7771, or of the cellular constituents, metabolites and/or secreted molecules of said strain, or of a composition comprising same, for the prevention and/or treatment of alterations such as excess weight, obesity, adipocyte hypertrophy, hepatic steatosis or fatty liver, dyslipidemia, hyperglycemia, insulin resistance and diabetes, metabolic syndrome, hypertension, cardiovascular diseases, dysfunction of the immune system, reduced defenses against infections, and imbalance in the composition of the intestinal microbiota.

8 Claims, 8 Drawing Sheets

(56) References Cited

OTHER PUBLICATIONS

Karlsson et al., Diet-induced obesity impairs the T cell memory response to influenza virus infection, J. Immunol., 184(6):3127-33 (2010).

Konturek et al., Brain-gut axis and its role in the control of food intake, J. Physiol. Pharmacol., 55(1 Pt. 2):137-54 (2004).

La Cava et al., The weight of leptin in immunity, Nat. Rev. Immunol., 4(5):371-9 (2004).

Ley et al., Microbial ecology: human gut microbes associated with obesity, Nature, 444(7122):1022-3 (2006).

Macia et al., Genes involved in obesity: Adipocytes, brain and microflora, Genes Nutr., 1(3-4):189-212 (2006).

Macia et al., Impairment of dendritic cell functionality and steady-state number in obese mice, J. Immunol., 177(9):5997-6006).

Nadal et al., Shifts in clostridia, bacteroides and immunoglobulin-coating fecal bacteria associated with weight loss in obese adolescents, Int. J. Obes. (Lond.), 33(7):758-67 (2009).

Samuel et al., A humanized gnotobiotic mouse model of host-archaeal-bacterial mutualism, Proc. Natl. Acad. Sci. USA, 103(26):10011-6 (2006).

Sanchez et al., Influence of environmental and genetic factors linked to celiac disease risk on infant gut colonization by *Bacteroides* species, Appl. Environ. Microbiol., 77(15):5316-23 (2011).

Sanz et al., 3rd International Immunonutrition Workshop, Session 8: Probiotics in the defence and metabolic balance of the organism, Gut microbiota in obesity and metabolic disorders, Proc. Nutr. Soc., 14:1-8 (2010).

Tilg et al., Adipocytokines: mediators linking adipose tissue, inflammation and immunity, Nat. Rev. Immunol., 6(10):772-83 (2006).

Varady et al., Degree of weight loss required to improve adipokine concentrations and decrease fat cell size in severely obese women, Metabolism, 48(8):1096-101 (2009).

Verwaerde et al., Influence of high-fat feeding on both naive and antigen-experienced T-cell immune response in DO10.11 mice, Scand. J. Immunol., 64(5):457-66 (2006).

Zhou et al., Signaling mechanisms involved in altered function of macrophages from diet-induced obese mice after immune responses, Proc. Natl. Acad. Sci. USA, 106(26):10740-5 (2009).

\* cited by examiner

SEQUENCE LISTING

<160> NUMBER OF SEQ ID NOS: 6

<210> SEQ ID NO 1
<211> LENGTH: 1335
<212> TYPE: DNA
<213> ORGANISM: Bacteroides uniformis
<220> FEATURE:
<221> NAME/KEY: misc_feature
<223> OTHER INFORMATION: Gene sequence of the ribosomal RNA16S from
      Bacteroides uniformis CECT 7771

<400> SEQUENCE: 1

```
agtcgagggg cagcatgaac ttagcttgct aagtttgatg gcgaccggcg cacgggtgag      60
taacacgtat ccaacctgcc gatgactcgg ggatagcctt tcgaaagaaa gattaatacc     120
cgatggcata gttcttccgc atggtagaac tattaaagaa tttcggtcat cgatggggat     180
gcgttccatt aggttgttgg cggggtaacg gcccaccaag ccttcgatgg ataggggttc     240
tgagaggaag gtcccccaca ttggaactga gacacggtcc aaactcctac gggaggcagc     300
agtgaggaat attggtcaat ggacgagagt ctgaaccagc caagtagcgt gaaggatgac     360
```

```
tgccctatgg gttgtaaact tcttttatac gggaataaag tgaggcacgy gtgcctttt      420
gtatgtaccg tatgaataag gatcggctaa ctccgtgcca gcagccgcgg taatacggag    480
gatccgagcg ttatccggat ttattgggtt taaagggagc gtaggcggac gcttaagtca    540
gttgtgaagt ttgcggctca accgtaaaat tgcagttgat actgggtgtc ttgagtacag    600
tagaggcagg cgcaattcgt ggtgtagcgg tgaaatgctt acatatcacg aagaactccg    660
attgcgaagg cagcttgctg gactgtaact gacgctgatg ctcgaaagtg tgggtatcaa    720
acaggattag ataccctggt agtccacaca gtaaacgatg aatactcgct gtttgcgata    780
tacagtaagc ggccaagcga aagcgttaag tattccacct ggggagtacg ccggcaacgg    840
tgaaactcaa aggaattgac gggggcccgc acaagcggag gaacatgtgg tttaattcga    900
tgatacgcga ggaaccttac ccgggcttga attgcaactg aatgatgtgg agacatgtca    960
gccgcaaggc agttgtgaag gtgctgcatg gttgtcgtca gctcgtgccg tgaggtgtcg   1020
gcttaagtgc cataacgagc gcaacccttg tcgatagtta ccatcaggtt atgctgggga   1080
ctctgtcgag actgccgtcg tgagatgtga ggaaggtggg gatgacrtca aatcascacg   1140
gsccttacrt ccggggctac acacgtgtta caatgggggg tacagaaggc agctacacgg   1200
cgacgtgatg ctaatcccta aagcctctct cagttcggat tggagtctgc aacccgactc   1260
catgaagctg gattcgctag taatcgcgca tcagccacgg cgcggtgaat acgttcccgg   1320
gtcttgtaca caccg                                                    1335

<210> SEQ ID NO 2
<211> LENGTH: 20
<212> TYPE: DNA
<213> ORGANISM: Artificial Sequence
<220> FEATURE:
<223> OTHER INFORMATION: Sequence of primer 27F

<400> SEQUENCE: 2
agagtttgat cctggctcag                                                 20

<210> SEQ ID NO 3
<211> LENGTH: 17
<212> TYPE: DNA
<213> ORGANISM: Artificial Sequence
<220> FEATURE:
<223> OTHER INFORMATION: Sequence of primer 1401r

<400> SEQUENCE: 3
cggtgtgtac aagaccc                                                    17

<210> SEQ ID NO 4
<211> LENGTH: 16
<212> TYPE: DNA
<213> ORGANISM: Artificial Sequence
<220> FEATURE:
<223> OTHER INFORMATION: Sequence of primer 530f

<400> SEQUENCE: 4
gtgccagcag ccgcgg                                                     16

<210> SEQ ID NO 5
<211> LENGTH: 17
<212> TYPE: DNA
<213> ORGANISM: Artificial Sequence
<220> FEATURE:
<223> OTHER INFORMATION: Sequence of primer U-968f

<400> SEQUENCE: 5
```

```
aacgcgaaga accttac                                                    17

<210> SEQ ID NO 6
<211> LENGTH: 15
<212> TYPE: DNA
<213> ORGANISM: Artificial Sequence
<220> FEATURE:
<223> OTHER INFORMATION: Sequence of primer M13

<400> SEQUENCE: 6
gagggtggcg gttct                                                      15
```

BACTEROIDES CECT 7771 AND THE USE THEREOF IN THE PREVENTION AND TREATMENT OF EXCESS WEIGHT, OBESITY AND METABOLIC AND IMMUNOLOGICAL ALTERATIONS

CROSS-REFERENCE TO RELATED APPLICATIONS

This U.S. patent application is a national stage application under 35 U.S.C. §371 of international application PCT/ES2013/070309, filed May 16, 2013, and claims the benefit of priority under 35 U.S.C. §119 of Spanish Patent Application No. 201230796, filed May 25, 2012, the entire content of which is hereby incorporated by reference for all purposes.

TECHNICAL FIELD

The present invention falls within the field of pharmaceuticals and food. Specifically, the present invention relates to the *Bacteroides uniformis* CECT 7771 strain, to its cellular components, metabolites and secreted molecules, and to compositions which, comprising at least one of the foregoing products, can also comprise other microorganisms or other compounds with biological activity. Likewise, the present invention also relates to the use of a *B. uniformis* strain or to the use of the CECT 7771 strain in the prevention and/or treatment of alterations such as excess weight, obesity, hepatic steatosis or fatty liver, dyslipidemia and, in particular, hypercholesterolemia and/or hypertriglyceridemia; hyperglycemia, insulin resistance and diabetes, preferably Type 2 diabetes mellitus and gestational diabetes; metabolic syndrome, hypertension, cardiovascular diseases, immune system dysfunction associated or not associated with these pathologies, preferably inflammation in peripheral tissues (adipose and pancreas) and reduced defense against infections, and imbalance in the composition of the intestinal microbiota.

BACKGROUND

Excess weight and obesity currently constitute one of the major public health concerns due to their increasing prevalence and comorbidities. These include, for example, dyslipidemia, diabetes, cardiovascular diseases, arteriosclerosis, hepatic steatosis or fatty liver, metabolic syndrome, hypertension and some types of cancer.

Hepatic steatosis or non-alcoholic fatty liver is an alteration with a high degree of association with obesity and appears in up to 50% of obese individuals, both children and adults, constituting the main current liver disease. Likewise, dyslipidemias (hypertriglyceridemia and hypercholesterolemia) are associated with obesity, Type 2 diabetes mellitus and hypertension, and constitute the main risk factor for cardiovascular pathologies. Lowering triglyceride and cholesterol levels in the serum of subjects with abnormally high levels of these biochemical parameters is beneficial and, particularly, lowering LDL cholesterol, as it is considered a clear risk factor for cardiovascular pathologies and a decrease therein is related to a reduction in morbidity and total mortality as a result of long-term cardiovascular pathologies. In this context, the liver plays an important role because it is the main organ principally responsible for maintaining cholesterol homeostasis (maintenance of physiological concentrations). The liver synthesizes 15% of novo cholesterol and this process is, in turn, regulated by dietary cholesterol. Cholesterol levels are maintained at a constant level by means of various mechanisms, including (i) regulation of the activity and concentration of the 3-hydroxy-3-methylglutaryl coenzyme A (HMG-CoA) reductase enzyme, (ii) regulation of the acyl-CoA:cholesterol acyltransferase (ACAT) enzyme, which controls excess intracellular free cholesterol and its transformation into cholesterol esters, which is the form in which they are transported, and (iii) regulation of the expression of the hepatic LDL receptors which allow absorption of plasma cholesterol and reverse transport thereof by HDL. The cholesterol just created in the liver is initially released into the bloodstream in the form of very low-density lipoproteins (VLDL) and can contribute to the increase thereof. However, the liver also contributes to the elimination of blood cholesterol through several mechanisms: (i) conversion into bile acids, (ii) transport of excess cholesterol to the intestine for faecal excretion and (iii) conversion of VLDL to LDLc and TG, which shall be used as sources of energy for extra-hepatic tissues. Alterations in lipid metabolism that affect the blood lipid profile and their accumulation in peripheral tissues can also occur in non-obese subjects, preceding obesity, or occur for causes other than obesity, including those of genetic (e.g: congenital diseases), infectious (for example, viral hepatitis), self-immune or nutritional origin (for example, malnutrition) or those arising from other clinical situations or pharmacological treatments (for example, use of drugs).

Obesity is also considered a state of mild chronic inflammation, characterised in that there is a high production of cytokines, adipokines and other pro-inflammatory proteins in the adipose tissue and in other peripheral tissues and at systemic level, that contribute to the metabolic alterations which can be permanently suffered by these individuals, such as Type 2 diabetes mellitus and cardiovascular pathologies (Tilg y Moschen, 2006. Nat Rev Immunol., 6: 772-783). The inflammatory factors related to obesity and metabolic alterations include, most notably, pro-inflammatory cytosine TNF-α. In particular, TNF-α reduces the expression of the genes involved in the action of insulin (for example, that of the insulin receptor gene), attenuates insulin signalling and inhibits lipoprotein lipase activity stimulated by the insulin. This favours the development of insulin resistance and hepatic steatosis. The function of the pro-inflammatory cytokines in this process is also evident in the use of drugs based on anti-TNF-α to improve pathologies such as hepatic steatosis and Type 2 diabetes mellitus (Tilg y Moschen, 2006. Nat Rev Immunol., 6: 772-783).

Obesity is also characterised by alterations in the functions of various immune system cells, such as macrophages, dendritic cells and T cells, associated with reduced defenses against pathogens and other antigens, and with a higher risk of infections and post-operative complications. Adipose tissue macrophages have less phagocytic capability and reduced respiratory burst, which are processes involved in the innate immune system's response to infectious agents (Zhou et al., 2009. Proc Natl Acad Sci USA, 106(26): 10740-5.). Additionally, dendritic cells have reduced capability to stimulate T cells, which are involved in the adaptive immune response responsible, for example, for antibody production in vaccination and for memory T cell response to infection (Karlsson et al., 2010. J Immunol., 184:3127-33).

Social changes associated with the steady increase in intake of high-energy-dense food and a low level of physical activity are considered to be the main causes of the increase in global obesity rates. However, traditional treatments based on hypocaloric diets and increased physical activity are less effective at controlling obesity and, in general, lead to limited and temporary weight loss. Neither has the use of pharmacological strategies been satisfactory, as they entail side effects. Consequently, the search for new intervention strategies aimed at improving the treatment and enabling the prevention of these pathologies continues.

The microbiota that colonise the human intestine are considered a new factor involved in obesity and associated diseases through their capability to regulate the individual's metabolic and immunological functions (Sanz et al., 2010. Proc Nutr Soc, 14: 1-8.). In recent years, various studies have established an association between an increase in the proportion of members of the phylum Bacteroidetes and a thin phenotype or weight loss and, on the contrary, a decrease therein has been associated with an obese phenotype (Ley et al., 2006. Nature, 444: 1022-1023; Nadal et al., 2008. Int J Obes., 33(7): 758-67); however, direct evidence of the possible effect of strains of the genus *Bacteroides* or of strains of the species *Bacteroides uniformis* administered orally in obesity has not been provided. Patent WO/2008/076696 proposes the use of changes in the intestinal microbiota to diagnose obesity and modification thereof as a way of treating obesity by increasing the proportion of the phylum Bacteroidetes and reducing that of the phylum Firmicutes. However, these phylogenetic groups integrate more than 90 and 200 different species and subspecies, respectively, whose individual effects could be very different and contradictory. In fact, WO/2008/076696 does not prove that no specific species or strain of the phylum *Bacteroides* has a beneficial effect in this context and, on the contrary, the only species evaluated in animal models, *Bacteroides thetaiotaomicron*, causes increase in body weight and adipose tissue and insulin resistance (Samuel y Gordon. Proc Nati Acad Sci USA. 2006; 27; 103(26): 10011-6). Patent US 2009/01 10664A1 proposes the use of the genus *Bacteroides* in body weight loss, but administering the bacterium after cleansing or removing the components themselves from the intestinal tract, as opposed to the present invention. Additionally, this patent does not disclose the results of the effects of any species or strain of this genus on body weight.

Other strategies based on the use of certain food ingredients or supplements only partially address the problem of obesity or of the pathologies arising from alterations in lipid and glucose metabolism, as in the case of stanols and phytosterols, which only act by reducing absorption of dietary cholesterol, which is not the only cause of elevation in plasma cholesterol. Likewise, lipid-lowering drugs such as statins that inhibit endogenous cholesterol synthesis do not achieve the required effectiveness due to being monotherapies focused on a single mechanism of action.

Therefore, the problem of finding specific components of commensal intestinal microbiota which can be used to prevent and/or treat diseases such as excess weight, obesity and metabolic pathologies associated or not associated to obesity and related to alterations in lipid and glucose metabolism, such as for example dyslipidemia, hepatic steatosis, metabolic syndrome, insulin resistance, Type 2 diabetes mellitus, gestational diabetes, hypertension and cardiovascular pathologies, in a more suitable manner by acting jointly on the immune system and metabolism alterations, responsible for chronic pathologies, remains unsolved.

DETAILED DESCRIPTION

The present invention relates to the strain *Bacteroides uniformis* CECT 7771, to the cellular components, metabolites, molecules secreted by said strain and combinations thereof; and to the compositions comprising at least one of the aforementioned products and which can comprise other microorganisms and/or other bioactive components, as well as to their use in the prevention and/or treatment of excess weight and/or obesity, and of the associated metabolic alterations, such as dyslipidemia, hepatic steatosis, insulin resistance and diabetes, metabolic syndrome, hypertension, cardiovascular diseases or immune system dysfunction with consequences on these or other pathologies such as infections. The present invention also relates to the use of said strain to prevent and/or treat these alterations when not associated to a problem of excess weight and/or obesity.

The CECT 7771 strain belonging to the species *B. uniformis*, has comparatively more favourable immunological properties than other strains of the same species and other species of the genus *Bacteroides*. The CECT 7771 strain induces significantly less production of pro-inflammatory cytokine TNF-α in macrophages than other strains of the same genus that form part of human intestinal microbiota, except *B. dorei* SS1 and *B. thetaiotaomicrom* SAC4, where the differences do not become significatives (Example 2, Table 1). The strain CECT 7771 also induces greater synthesis of anti-inflammatory cytokine IL-10 than the other evaluated strains (Example 2, Table 1). Other evaluated strains of the same species (β. *uniformis*) induced a significantly higher proportion of the TNF-α/IL-10 ratio than the strain object of the patent (CECT 7771), indicating that the balance of pro- and anti-inflammatory cytokines induced by the latter is more favourable than that induced by the other strains (Example 2, Table 1). As argued in the section on the state of the art, the synthesis of TNF-α by macrophages has been directly linked to obesity, dyslipidemia, hepatic steatosis, diabetes, hypertension and the risk of cardiovascular pathologies. The capability of the strain of the invention to increase synthesis by means of anti-inflammatory cytokine IL-10 is also a relevant property because it can contribute to reduce the chronic inflammation associated with obesity and metabolic alterations. Studies conducted on hepatocytes also indicate that the CECT 7771 strain reduces the accumulation of triglycerides and cholesterol and improves sensitivity to insulin and to the use of glucose in comparison with other species of the genus *Bacteroides* and with other strains of the species *B. uniformis* (Example 2, FIG. 1). All of these results show the greater suitability of the strain object of the patent to control inflammation and lipid and glucose metabolism than other species and strains of the genus *Bacteroides*. Studies conducted by our group also reveal that breastfeeding promotes an increase in the prevalence of the species object of the patent (β. *uniformis*) in the microbiota of children in the early stages of life but not in those subjected to artificial feeding (Sanchez et al. 2011. Appl Environ Microbiol. 2011; 77(15):5316-23) and, in turn, breastfeeding protects them against the development obesity and metabolic alterations.

Globally, the results obtained with macrophage and hepatocyte cultures indicate that the species *B. uniformis* is particularly suited for use in these pathologies, in comparison to the rest of the species found in humans that do not have these properties (for example, but not limited to, *B. thetaiotaomicron*) and, in particular, the strain *B. uniformis* CECT 7771.

In addition to the specific selection of the strain object of the invention and as opposed to the state of the art, the present invention addresses the treatment of obesity from a multifactorial perspective and acts on new key targets for preventing and/or treating this pathology and other metabolic alterations associated or not associated to obesity, not described for any known strain of the species *Bacteroides*

*uniformis*. The most interesting fact is that none of the known strains of this species has proven to be useful in the simultaneous and effective treatment of all the pathologies indicated throughout the present invention.

Therefore, the present invention contributes a highly valuable strain of the species *B. uniformis* to the state of the art for treating excess weight and/or obesity, in addition to certain pathologies such as, for example, but not limited to, hepatic steatosis, dyslipidemia, insulin resistance, diabetes, metabolic syndrome, hypertension or cardiovascular diseases associated or not associated with obesity. Likewise, the present invention contributes a strain of the species *B. uniformis* to the state of the art that improves immune system alterations and, in particular, the inflammation of the peripheral tissues associated with the aforementioned chronic pathologies and reduced defenses against infections, in addition to restoring the composition of the intestinal microbiota, which also contributes to the aforementioned pathologies.

Essentially, the advantages of using the strain *B. uniformis* CECT 7771 of the present invention are the following:

Administration of the strain object of the invention produces a reduction in body weight in obese subjects (Example 3, Table 2).

Administration of the strain object of the invention gives rise to a reduction in fat accumulated in the liver in obese and non-obese subjects (Example 3, FIG. 2). Specifically, in normal-weight subjects the strain *B. uniformis* CECT 7771 produces an increase in the number of hepatocytes without steatosis (grade 0) and a decrease in the number of hepatocytes with steatosis grade 1 and 2. In obese subjects the strain produces an increase in the number of hepatocytes with a lower grade of steatosis (grade 0 and 1) and a decrease in the number of hepatocytes with a higher grade of steatosis (grade 2 and 3); however, in obese subjects to which the strain is not administered, the proportion of the type of hepatocytes is reversed, with a predominance of those with maximum fat content. This demonstrates that the administration of the strain reduces the total accumulation of fat in the liver, induced or not induced dietetically. Histology sections of hepatic tissue also demonstrated these effects (Example 3, FIG. 2). The strain *B. uniformis* CECT 7771 also reduces triglyceride and cholesterol levels in the liver in obese subjects (Example 3, Table 2).

Administration of the strain *B. uniformis* CECT 7771 produces a reduction in adipocyte size in obese subjects (Example 3, FIG. 3). In particular, administration of the strain CECT 7771 to animals gives rise to an increase in small-sized adipocytes (<2000 µm$^2$) at the expense of a decrease in larger-sized adipocytes in epidydimal tissue, while all large-sized adipocytes (>2000-7000 µm$^2$) in obese animals to which the strain was not administered increased (Example 3, FIG. 3). Histology sections of the adipose tissue also demonstrated these effects (Example 3, FIG. 3).

The fact that the CECT 7771 strain reduces the size of the adipocytes demonstrates that it is useful for treating adipocyte hypertrophy, which is maintained over time and occurs in a large number of adipocytes, can cause excess weight and obesity and insulin resistance. This is because larger-sized adipocytes secrete a higher concentration of growth factors that trigger adipogenesis through the differentiation of pre-adipocytes, generating a feedback process. Additionally, hypertrophic adipocytes produce an abnormally high concentration of inflammatory cytokines and chimiokines (TNF-α, MCP-1, resistin, etc.) that inhibit insulin signalling in the hepatocytes and give rise to insulin resistance and alter the corporal distribution of lipids. For example, an increase in adipocyte size is also related to hepatic fatty acid intake, which gives rise to hepatic steatosis and its complications. Therefore, the strain can also contribute to preventing or improving these associated pathologies.

The *B. uniformis* CECT 7771 strain reduces the number of fat globules in the enterocytes, i.e. it reduces the amount of dietary fat that can be absorbed and passed to the lymphatic system and bloodstream in the form of chylomicrons and, thus, to peripheral tissues (Example 3, FIG. 4).

The increased absorption of dietary fat, in addition to giving rise to excess weight and/or obesity on causing an increase in the accumulation thereof in adipose tissues, can be associated with other pathologies without causing excess weight or obesity, such as for example, and without limiting the scope of the invention, dyslipidemia, metabolic syndrome, arterial hypertension, cardiovascular pathologies and other alterations arising from the relationship between lipid and glucose metabolism. Therefore, the CECT 7771 strain can be effective in the prevention and/or treatment of diseases related to the excessive absorption of dietary fat.

The *B. uniformis* CECT 7771 strain reduces dyslipidemia and, in particular, peripheral blood triglyceride and cholesterol levels in obese subjects (Example 3, Table 2), thereby reducing the risk of developing cardiovascular diseases. This effect could be partially due to the strain's capability to inhibit the amount of dietary fat absorbed.

Dyslipidemia can also be a consequence not only of absorbed dietary fat but also of other metabolic alterations such as adipocyte insulin resistance which, without being necessarily associated with obesity, causes the adipocytes to release fatty acids that will be used in the liver for triglyceride and cholesterol synthesis, and can also be secreted and their concentration in peripheral blood increased. Dyslipidemia can also appear in subjects with a genetic predisposition to develop this metabolic alteration, without necessarily being associated with obesity, with insulin resistance or an increase in the absorption of dietary fat. Therefore, the CECT 7771 strain can be effective in the prevention and/or treatment of dyslipidemia (for example, hypertriglyceridemia and hypercholesterolemia) and related pathologies, such as hypertension and cardiovascular pathologies.

The *B. uniformis* CECT 7771 strain reduces serum glucose in parallel to fasting insulin and resistance to insulin index HOMA (Homeostasis Model Assessment), which makes it possible to estimate insulin resistance (a high index indicates low insulin sensitivity) and pancreatic beta-cell function. Additionally, the strain object of the invention reduces postprandial glycemic response after ingestion of oral glucose, which also indicates an improvement in glucose metabolism and insulin sensitivity (Example 3, Table 2). The strain object of the invention also reduces adipokine leptin concentrations in obese subjects, indicating an improvement in the metabolic function of said adipokine, which in turn can contribute to improving glucose metabolism and insulin production or sensitivity (Example 4, Table 3).

An increase in serum concentrations of glucose, due to the development of insulin resistance, is frequently associated with excess weight and obesity, although it can also occur in the absence of obesity, and can lead to the development of Type 2 diabetes mellitus and gestational diabetes. Therefore, the CECT 7771 strain can be effective in the prevention and/or treatment of related glucose metabolism alterations that can lead to the development of insulin resistance and, finally, diabetes.

The CECT 7771 strain is capable of reducing the synthesis of pro-inflammatory proteins in peripheral tissue in normal-weight subjects treated with said strain with respect to those not treated with said strain. Therefore, the strain object of the invention reduces the synthesis of the inflammatory cytokine TNF-α and increases the synthesis of the inflammatory cytokine IL-10 in adipose tissue, while the levels of this cytokine decreases in obese subjects not treated with the strain. TNF-α synthesis increases with obesity and other pathologies and contributes to the development of insulin and leptin resistance, inhibiting its anorexigenic effects (reduction in the sense of hunger) and its function in the regulation of body weight and lipid and glucose metabolism (Example 4, Table 3). Additionally, the strain object of the invention reduces the concentration of the inflammatory cytokine TNF-α in the pancreas, improving the function of this organ in the regulation of glucose metabolism (Example 4, Table 3). The strain object of the invention also reduces the concentration of adipokine leptin, which can also favour inflammation in the context of excess weight and obesity (Example 4, Table 3).

Therefore, the CECT 7771 strain regulates the production of cytokines and adipokines, whose synthesis is altered in the case of obesity and in certain diseases associated therewith, such as for example, but not limited to, dyslipidemia, metabolic syndrome, insulin resistance, hypertension, cardiovascular diseases and steatosis, both in peripheral blood and in tissues, and in other diseases not necessarily associated with excess weight and/or obesity and, therefore, can be used in the treatment and prevention of these pathologies.

The CECT 7771 strain improves innate and adaptive immune system cell function, increasing their capability to respond to infectious agents, antigens or allergens in obese and non-obese subjects. In particular, the administration of the strain to animal models of obesity induced by a fat-rich diet improves, inter alia, macrophage function in phagocytosis and in cytokine synthesis in response to pathogen stimuli (Example 4, FIG. 5). The strain object of the invention also improves adaptive immune system dendritic cells and Ts cell function (Example 4, FIG. 6).

Therefore, the CECT 7771 strain has an additional positive effect because it can be useful in the prevention and treatment of infections and improvement in protective responses, for example in vaccination and immunisation processes, due to the fact that these immune system functions are altered in subjects with excess weight and obesity. Additionally, the strain of the invention can be useful in the treatment or prevention of other diseases accompanied by immunosuppression (essentially of macrophages, dendritic cells and T cells), associated or not associated with obesity and excess weight, as these effects are also demonstrated in non-obese subjects.

The CECT 7771 strain also restores the composition of the intestinal microbiota, normalising the alterations associated with excess weight and obesity (reduced abundance of the group C. coccoides of the genus *Bifidobacterium* and increased abundance of the Enterobacteriaceae family) and attenuating the inflammatory effect caused by said alterations, and which has been related to weight gain, insulin resistance, metabolic endotoxemia, hepatic steatosis and alterations of the intestinal barrier (Example 4, Table 4 and Example 3, FIG. 7). The strain of the invention also increases the number of *Bacteroides* spp. and *Bifidobacterium* spp. in normal-weight subjects and can be used to restore these microbial populations in the intestine, which may be altered due to conditions other than obesity and excess weight. Therefore, the CECT 7771 strain is also applicable in the prevention and treatment of diseases associated with alterations of the intestinal microbiota and *Enterobacter* infections.

One aspect of the present invention relates to a *B. uniformis* strain with deposit number CECT 7771. Said strain was deposited with the Spanish Type Culture Collection (CECT) on 21 Jul. 2010 and assigned deposit number CECT 7771. The address of said international deposit Authority is: Universidad de Valencia/Edificio de investigación/Campus de Burjassot/46100 Burjassot (Valencia, Spain).

The scientific classification of the CECT 7771 strain of the present invention is: Kingdom: Bacteria/Phylum: Bacteroidetes/Order: Bacteroidales/Family: Bacteroidaceae/Genus: *Bacteroides*/Species: *uniformis*.

The characteristics of said strain are the following:
The substrates oxidised or fermented by the *B. Uniformis* CECT 7771 strain are: lactose, sucrose, maltose, salicin, xylose, arabinose, esculin, cellobiose, mannose and raffinose.

The *B. uniformis* CECT 7771 strain grows in a temperature range between 31 and 42° C., with an optimum at 37° C.

Additionally, the *B. uniformis* CECT 7771 strain is stable under conditions of gastrointestinal stress (acid pH and high concentration of bile). Its viability after incubation under gastric conditions (3 g/l pepsin at pH 3 and 2.5) during average gastric emptying time (2 h) is 50-70% and, after incubation in the presence of bile salts (0.5 and 1%), remains above 90%. It is also resistant to the conditions of technological preservation processes (freezing, freeze drying, etc.) and food processing conditions (cooling, freeze drying, fermentation, etc.). All of these properties guarantee its viability and persistence and effectiveness in the intestine.

Another aspect of the present invention relates to a strain derived from the *B. uniformis* CECT 7771 strain, wherein said strain maintains or improves the capabilities described throughout the present invention. The microorganism derived can be naturally occurring or produced intentionally by mutagenesis methods known in the prior art such as, but not limited to, growth of the original microorganism in the presence of mutagenic agents or stressors, or directed genetic engineering of specific genes. According to a preferred embodiment, the strain derived from the *B. uniformis* CECT 7771 strain is a genetically modified mutant. The terms "mutant strain" or "derived strain" can be used interchangeably.

The *B. uniformis* CECT 7771 strain or any mutant or derivative thereof may be used in any way to exert the effects described, for example, according to a preferred embodiment of the present invention, the *B. uniformis* CECT 7771 strain is formed of viable cells (cultivable or uncultivable) or, according to another preferred embodiment of the invention, the strain is in the form of non-viable cells ("dead" cells inactivated by any technique known in the art, such as for example, but not limited to, heat, freezing or ultraviolet radiation).

Hereinafter, any of the bacterial strains of the previously described species *B. uniformis* (*B. uniformis* CECT 7771 strain or any mutant or derivative thereof) may be referred to as the "strain of the present invention" or the "strain of the invention."

Another aspect of the present invention relates to cellular components, metabolites, secreted molecules or any combination thereof, obtained from the strain of the invention or from a mixture of microorganisms comprising at least one strain of the invention.

The cellular components of the bacterium may include the components of the cell wall (such as, but not limited to, peptidoglican), nucleic acids, membrane components, or others such as proteins, lipids and carbohydrates and combinations thereof, such as lipoproteins, glycolipids or glicoproteins. The metabolites include any molecule produced or modified by the bacterium as a consequence of their metabolic activity during growth, their use in technological processes (for example, but not limited to, food or drug elaboration processes) during product storage or during gastrointestinal transit. Examples of these metabolites are, but not limited to, organic and inorganic acids, proteins, peptides, amino acids, enzymes, lipids, carbohydrates, lipoproteins, glycolipids, glycoproteins, vitamins, salts, metals or nucleic acids. The secreted molecules include any molecule exported or released by the bacterium during growth thereof, its use in technological processes (for example, preparation of food or drugs), product storage or gastrointestinal transit. Examples of these molecules include, but not limited to, organic and inorganic acids, proteins, peptides, amino acids, enzymes, lipids, carbohydrates, lipoproteins, glycolipids, glycoproteins, vitamins, salts, metals or nucleic acids.

Another aspect of the present invention relates to a composition comprising the strain of the invention, and/or cellular constituents, metabolites, molecules secreted by the strain of the invention or any previously defined combination thereof.

The composition, generally defined, is a set of components which is formed at least by the strain of the invention at any concentration, or at least by the cellular components, metabolites, molecules secreted by the strain of the invention or any of its combinations, or a combination thereof.

According to the invention, the previous composition may further comprise at least one additional microorganism other than the strain of the invention and/or its cellular components, metabolites or secreted molecules, or any combination thereof. For example, but not limited to, the additional microorganism that may form part of said composition is selected from among at least one of the following groups:
- at least one strain of another species of the genus *Bacteroides* or of the species *B. uniformis;*
- at least one lactic acid bacterium or intestinal *bifidobacterium*, of alimentary or environmental origin. The lactic bacterium is selected from the list comprising, but not limited to, bacteria of the genus *Bifidobacterium, Lactobacillus, Lactococcus, Enterococcus, Propionibacterium, Leuconostoc, Weissella, Pediococcus,* or *Streptococcus;*
- at least one strain of other phylogenetic groups, genera or species of intestinal prokaryotes of intestinal, alimentary or environmental origin, such as, but not limited to, *Archaea, Firmicutes, Bacteroidetes, Proteobacteria, Actinobacteria, Verrucomicrobia, Fusobacteria, Metanobacteria, Spirochaetes, Fibrobacteres, Deferribacteres, Deinococcus, Thermus, Cyanobacteria, Methanobrevibacterium, Peptostreptococcus, Ruminococcus, Coprococcus, Subdolingranulum, Dorea, Bulleidia, Anaerofustis, Gemella, Roseburia, Catenibacterium, Dialister, Anaerotruncus, Staphylococcus, Micrococcus, Propionibacterium, Enterobacteriaceae, Faecalibacterium, Bacteroides, Parabacteroides, Prevotella, Eubacterium, Akkermansia, Bacillus, Butyrivibrio,* or *Clostridium;*
- at least one strain of fungus or yeast such as, but not limited to, belonging to the genus *Saccharomyces, Candida, Pichia, Debaryomyces, Torulopsis, Aspergillus, Rhizopus, Mucor* or *Penicillium.*

Said additional microorganism may be a strain of the same species or different species or taxonomic group of microorganisms corresponding to the strain of the invention. The cells comprising the composition may be viable or non-viable, and be in any stage of development or growth (latent, exponential, stationary, etc.), regardless of their morphology. Preferably, said additional microorganism further comprises at least one intestinal bacterium or lactic bacterium.

Optionally, the composition according to any of those defined above may further comprise at least one bioactive component (active substance, active ingredient or therapeutic agent) such as, for example, other food, plant and/or pharmaceutical components.

The term "bioactive component" relates to a compound having biological activity in the scope of applicability of the patent that can enhance or supplement the activity of a strain of the species *B. uniformis* and preferably the CECT 7771 strain object of the invention, including food ingredients or components (such as but not limited to: poly-unsaturated fatty acids, conjugated linoleic acid, prebiotics, fibre, guar gum, glucomannan, chitosan picolinate, copper, calcium, etc.), plants, plant extracts or components (for example, but not limited to, polyphenols, ephedrine or *Ephedra* spp., green tea [*Camellia sinensis*], bitter orange [*Citrus aurantium*]), and drugs (for example, but not limited to, statins, orlistat, sibutramine, liraglutido etc.).

In a preferred embodiment, the composition as defined above is a pharmaceutical composition. The pharmaceutical composition is a set of components which is formed at least by the strain of the invention at any concentration, or at least by the cellular components, metabolites, molecules secreted by the strain of the invention or any combination thereof, having at least one application in improving the physical or physiological or psychological well-being of a subject, which implies an improvement in the general state of health or reduced risk of disease. Said pharmaceutical composition can be a drug.

The meaning of the term "drug" is more limited than the meaning of "pharmaceutical composition", as defined herein, as a drug necessarily implies a preventive or therapeutic effect. The drug to which the present invention relates may be for human or veterinary use. The "drug for human use" is any substance or combination of substances presented as having properties for treating or preventing diseases in human beings or that can be used in humans or administered to human beings either with a view to restoring, correcting or modifying physiological functions by exerting a pharmacological, immunological or metabolic action, or to making a medical diagnosis. The "drug for veterinary use" is any substance or combination of substances presented as having properties for curing or preventing animal diseases or which may be administered to animals with a view to restoring, correcting or modifying their physiological functions by exerting a pharmacological, immunological or metabolic action, or to make a veterinary diagnosis. "Veterinary drugs" shall also be considered a "premix for medicated feed" prepared for incorporation into feed.

In addition to the requirement of therapeutic effectiveness where said pharmaceutical composition may require the use of other therapeutic agents, there may be additional basic reasons that oblige or recommend using a combination of a compound of the invention and a bioactive component to a large extent, wherein said bioactive component is attributed an appropriate activity for constituting a drug. Said compound of the invention obviously relates to any of *Bacteroides uniformis* strains of the invention or to the cell components, metabolites, secreted molecules or any combination thereof, derived from one of the strains of the invention.

In a preferred embodiment, the pharmaceutical composition further comprises, at least, one vehicle and/or a pharmaceutically acceptable excipient.

The term "excipient" relates to a substance that aids the absorption of any of the components of the composition of the present invention, stabilises said components or aids the preparation of the pharmaceutical composition in the sense of giving consistency or contributing flavours that make it more enjoyable. Thus, excipients may have the function of holding the components together, such as starches, sugars or celluloses, a sweetening function, colouring function, drug protection function such as to isolate from the air and/or humidity, the function of filling a tablet, capsule or other form of presentation such as, for example, dibasic calcium phosphate, a disintegrating function to facilitate the dissolution of the components and their absorption in the intestine, without excluding any other type of excipients not mentioned in this paragraph. Therefore, the term "excipient" is defined as the material included in the galenic forms, is added to the active ingredients or their associations to enable their preparation and stability, modify their organoleptic properties or determine the physicochemical properties of the pharmaceutical composition and its bioavailability. A "pharmaceutically acceptable" excipient must allow the activity of the compounds of the pharmaceutical composition, i.e. to be compatible with said components.

The "galenic form or pharmaceutical form" is the provision to which the active ingredients and excipients are adapted to constitute a drug. It is defined by the combination of the form in which the pharmaceutical composition is presented by the manufacturer and the form in which it is administered.

The "vehicle" or carrier is preferably an inert substance. The function of the vehicle is to facilitate the incorporation of other compounds, allow better dosage and administration or give consistency and shape to the pharmaceutical composition. Therefore, the vehicle is a substance used in the drug to dilute the any of the components of the pharmaceutical composition of the present invention to a given volume or weight; or while not diluting said components, is capable of allowing better dosage and administration or giving the drug consistency and shape. When the form of presentation is liquid, the pharmaceutically acceptable vehicle is the diluent.

Additionally, the excipient and the vehicle must be pharmaceutically acceptable, i.e. the excipient and the vehicle is allowed and evaluated so as not to cause damage to the bodies to which it is administered.

In each case the galenic form of the pharmaceutical composition and, therefore, the drug, will be adapted to the dosage form used. Therefore, the composition of the present invention can be provided in the form of solutions or any other clinically permitted dosage form and in a therapeutically effective quantity. The pharmaceutical composition of the invention may be formulated in solid, semisolid, liquid or gaseous forms, such as tablet, capsule, powder, granule, ointment, solution, suppository, injection, inhalant, gel, microsphere or aerosol. According to an even more preferred embodiment of the present invention, the pharmaceutical composition is in a form adapted for oral administration.

The form adapted for oral administration relates to a physical state which would permit its oral administration. Said form adapted for oral administration is selected from the list comprising, but not limited to, drops, syrup, herbal tea, elixir, suspension, extemporaneous suspension, drinkable phial, tablet, capsule, granule, wafer, pill, tablet, lozenge, troche or lyophilised.

Alternatively, the pharmaceutical composition may also be presented in a form adapted for sublingual, nasal, intrathecal, bronchial, lymphatic, rectal, transdermal, inhaled or parenteral administration. The strain of the invention; the cellular components, metabolites, secreted molecules or any combination thereof, obtained from the strain of the invention, or the composition of the invention may, for example, be associated with, but not limited to, liposomes or micelles.

In the sense used in this description, the expression "therapeutically effective amount" relates to a certain amount of the component of the pharmaceutical composition which, when administered to a mammal, preferably a human, is sufficient to result in prevention and/or treatment, as defined later in the text, of a disease or pathological condition of interest in the mammal, preferably a human. Said component of the pharmaceutical composition relates to the strain of the invention; or to the cellular components, metabolites, secreted molecules; or a combination thereof, that may optionally be comprised in said composition in combination with an additional bioactive component, and contributing to the therapeutic effect of the pharmaceutical composition. The therapeutically effective amount will vary, for example, according to the activity of the strain of the invention; the additional microorganism or additional microorganisms comprising the composition of the invention, cellular components, metabolites, secreted molecules or any combination thereof, in any dosage form; the therapeutically effective amount will also vary according to the metabolic stability and duration of action of that compound; the patient's age, body weight, general state of health, sex and diet, the route and time of administration, the rate of excretion, drug combination; the severity of the particular alteration or pathological condition; and the subject undergoing therapy, but may be determined by a person skilled in the art based on their own knowledge and that description.

In another preferred embodiment, the composition defined according to the invention is a nutritional composition.

In a more preferred embodiment, the nutritional composition is selected from a food (which may be a food for specific nutritional purposes or a medicinal food), a supplement, a nutraceutical, a probiotic or a symbiotic.

The term "nutritional composition" of the present invention relates to a food that, regardless of providing nutrients to the subject eating it, has a beneficial effect on one or more bodily functions, so as to provide a better state of health and well-being. Accordingly, such nutritional composition may be destined for the prevention and/or treatment of a disease or for the reduction of disease risk factors.

The term "supplement", which is synonymous with any of the terms "dietary supplement", "nutritional supplement" or "food supplement" is a component or components destined for supplementing the diet and may be a food. Examples of dietary supplements are, but not limited to, vitamins, minerals, botanical products, amino acids and food components such as enzymes and glandular extracts. They are not presented as a substitute for a conventional food or as the sole component of a meal or diet, but rather as a dietary supplement.

The term "nutraceutical" as used herein relates to the isolated substances of a food used in dosage form and having a beneficial effect on human health. Said nutraceutical can be a supplement.

The term "probiotic" as used herein relates to microorganisms which, when administered in adequate amounts, have beneficial effects on the health of the host organism.

The term "symbiotic" as used herein relates to those foods which contain a mixture of prebiotics and probiotics. As a general rule, they contain a prebiotic component to enhance the growth and/or metabolic activity and, ultimately, the effect of the probiotic with which it is combined, such as for example, but not limited to, the association of fructooligosaccharides and galactooli-gosaccharides with an intestinal bacterium such as a strain of the species *B. uniformis*.

According to a more preferred embodiment of the foregoing, the food is selected from the list comprising: dairy product, vegetable product, meat product, snack, chocolate, baby food or drink. The dairy product is selected from the list comprising, but not limited to, fermented milk by-products (for example, but not limited to, yoghurt or cheese) or non-fermented milk by-products (for example, but not limited to, ice cream, butter, margarine, whey). The vegetable product is, for example, but not limited to, a grain in any form of presentation, fermented or non-fermented. The drink may be, but not limited to, any fruit juice or non-fermented milk.

Another more preferred embodiment of the present invention relates to any of the compositions described in the invention, wherein said composition has a concentration of the strain of between $10^3$ and $10^{14}$ colony-forming units (cfu) per gramme or milliliter of final composition. The concentration of the strain is the therapeutically effective or nutritionally effective concentration, as appropriate. The nutritional composition and the pharmaceutical composition may be formulated, but not limited to, in solid, semi-solid, liquid or gaseous forms, such as tablet, capsule, microcapsule, powder, granule, ointment, solution, paste, suppository, injection, inhalant, gel, microsphere or aerosol.

Hereinafter, reference may be made to any of the compositions, general composition, pharmaceutical composition or nutritional composition, defined in the preceding paragraphs using the term "composition of the present invention" or "composition of the invention."

Another aspect of the invention relates to the use of the strain of the invention; or the cellular component, metabolite, secreted molecule or any combination thereof, of the invention in the manufacture of a pharmaceutical composition, a drug or a nutritious composition.

Another aspect of the invention relates to a strain of the species *Bacteroides uniformis* for uses other than the treatment and/or prevention of excess weight or obesity. The present invention demonstrates how a strain of the species *Bacteroides uniformis* (such as the *B. uniformis* CECT 7771 strain) may be used to treat and/or prevent other lipid and glucose metabolism alterations, not necessarily associated with excess weight or obesity, such adipocyte hypertrophy; hepatic steatosis or fatty liver, dyslipidemia (for example, hypertriglyceridemia and/or hypercholesterolemia), hypertension, cardiovascular diseases, hyperglycaemia, insulin resistance and/or diabetes (for example, gestational diabetes or Type 2 diabetes mellitus); or metabolic syndrome. Likewise, it was observed that said strain of *Bacteroides uniformis* can be used to improve the function of the immune system, for example, reducing inflammation in peripheral tissues (adipose and pancreas) caused by the previously described chronic metabolic alterations, and to increase defenses against infection and the response to vaccination. In addition, the *Bacteroides uniformis* strain can be used to restore the composition of the intestinal microbiota and prevent pathologies related to the alteration thereof, for example, reducing the concentration of enterobacteria in intestinal contents.

In a preferred embodiment of use in medicine, a strain of *Bacteroides uniformis*; or one of its cellular components, metabolites, secreted molecules or a combination thereof; or a composition comprising any of the above, is used to reduce adipocyte size in a subject and, therefore, is also used in the treatment and/or prevention of adipocyte hypertrophy.

In another preferred embodiment of use in medicine, a strain of *Bacteroides uniformis*, or one of its cellular components, metabolites, secreted molecules or a combination thereof; or a composition comprising any of the above, is used to reduce the accumulation of fat in hepatocytes and, therefore, is also used in the treatment and/or prevention of hepatic steatosis or fatty liver.

In another preferred embodiment of use in medicine, a strain of *Bacteroides uniformis*, or one of its cellular components, metabolites, secreted molecules or a combination thereof; or a composition comprising any of the above, is used to reduce blood triglyceride and cholesterol levels and, therefore, is also used in the treatment and/or prevention of dyslipidemia, more preferably of a dyslipidemia selected from among hypertriglyceridemia and/or hypercholesterolemia.

In another preferred embodiment of use in medicine, a strain of *Bacteroides uniformis*, or one of its cellular components, metabolites, secreted molecules or a combination thereof; or a composition comprising any of the above, is used in the treatment and/or prevention of a cardiovascular disease.

In another preferred embodiment of use in medicine, a strain of *Bacteroides uniformis*, or one of its cellular components, metabolites, secreted molecules or a combination thereof; or a composition comprising any of the above, is used to reduce the blood glucose levels and, therefore, can also be used in the treatment and/or prevention of hyperglycemia and/or a pathology associated with higher levels of blood glucose amounts.

In another preferred embodiment of use in medicine, a strain of *Bacteroides uniformis*, or one of its cellular components, metabolites, secreted molecules or a combination thereof; or a composition comprising any of the above, is used in the treatment and/or prevention of insulin resistance and/or diabetes, and, more preferably, the diabetes is selected from among gestational diabetes or Type 2 diabetes mellitus.

In another preferred embodiment of use in medicine, a strain of *Bacteroides uniformis*, or one of its cellular components, metabolites, secreted molecules or a combination thereof; or a composition comprising any of the above, is used in the treatment and/or prevention of metabolic syndrome.

In another preferred embodiment of use in medicine, a strain of *Bacteroides uniformis*, or one of its cellular components, metabolites, secreted molecules or a combination thereof; or a composition comprising any of the above, is used in the treatment and/or prevention of hypertension.

In another preferred embodiment of use in medicine, a strain of *Bacteroides uniformis*, or one of its cellular components, metabolites, secreted molecules or a combination thereof; or a composition comprising any of the above, is used to improve the function of the immune system of a subject with respect to an untreated control.

Among the improvements of immune function, a strain of *Bacteroides uniformis*, or one of its cellular components, metabolites, secreted molecules or a combination thereof; or a composition comprising any of the above, can reduce inflammation in peripheral tissues that causes the chronic metabolic alterations object of the patent including, inter alia, dyslipidemia, hepatic steatosis, adipocyte hypertrophy, insulin resistance and diabetes, hypertension, metabolic syndrome and cardiovascular diseases. Also, another enhancement of the immune system provided by a strain of *Bacteroides uniformis* is its ability to stimulate responses of immunocompetent cells (macrophages, dendritic cells and lymphocyte T-cells) and, thus, defenses against pathogens and antigens.

In another preferred embodiment of use in medicine, a strain of *Bacteroides uniformis*, or one of its cellular components, metabolites, secreted molecules or a combination thereof; or a composition comprising any of the above, is used to reduce inflammation in peripheral tissues, preferably adipose and/or pancreatic tissue.

In another preferred embodiment of use in medicine, a strain of *Bacteroides uniformis*, or one of its cellular components, metabolites, secreted molecules or a combination thereof; or a composition comprising any of the above, is used in the treatment and/or prevention of infection and/or to improve the response to vaccination. The examples show how a strain of *B. uniformis* improves the function of the innate and adaptive immune system against pathogens and antigens, therefore improving the response to infection of an individual to whom it is administered.

In another preferred embodiment of use in medicine, a strain of *Bacteroides uniformis*, or one of its cellular components, metabolites, secreted molecules or a combination thereof; or a composition comprising any of the above, is used to restore the composition of the intestinal microbiota and, preferably, to reduce the concentration of potential pathogens, such as enterobacteria in the intestinal contents of a subject with respect to an untreated control.

According to the present description, a strain of *Bacteroides uniformis*, or one of its cellular components, metabolites, secreted molecules or a combination thereof; or a composition comprising any of the above, for use in the treatment and/or prevention of different diseases or metabolic alterations, to improve the function of the immune system or to reduce the concentration of enterobacteria, can obviously be understood as a method for treating and/or preventing such diseases or alterations, or a method for improving the function of the immune system, or a method for reducing the concentration of enterobacteria, which comprises administering a therapeutically effective amount of said strain to a subject. Likewise, the present invention also protects the use of said strain; or its cellular components, metabolites, secreted molecules, or a combination thereof, for the manufacture of a nutritional composition, a pharmaceutical composition or a drug for the treatment and/or prevention of such diseases or metabolic alterations, for improving the function of the immune system or for reducing the concentration of enterobacteria.

Another aspect of the invention relates to the strain of the invention, or the cellular component, metabolite, secreted molecule or any combination thereof of the invention; or the composition of the invention for use in medicine.

The term "treatment", as understood herein, relates to fight the effects of a disease or pathological condition of interest in a subject (preferably a mammal and, more preferably, a human) that includes:

(i) inhibiting the disease or pathological condition, i.e. arresting its development;
(ii) relieving the disease or the pathological condition, i.e. causing regression of the disease or the pathological condition or its symptoms;
(iii) stabilizing the disease or pathological condition.

The term "prevention" as understood in the present invention consists of preventing the onset of the disease, that is, preventing the disease or pathological condition from occurring in a subject (preferably a mammal and, more preferably, a human), particularly when said subject is predisposed to develop the pathological condition.

The term "excess weight" relates to a disease characterised in that the subject has a body mass index (BMI) equal to or greater than 25. BMI is a measure of association between the weight and height of an individual. BMI is calculated using the following formula: Mass $(kg)/height^2$ $(m)$. Excess weight is characterised by a BMI of ≥25 to <30.

The term "obesity" relates to a disease characterised in that the subject has a BMI equal or greater than 30. Obesity is classified into different levels, considering that subjects having a BMI>40 have morbid obesity. Other parameters used to determine if an individual has central obesity are the absolute waist circumference (subject is obese when >102 cm in men [central obesity] and >88 cm in women) or the waist-hip ratio (the subject is obese when >0.9 for men and >0.85 for women). An alternative way to determine obesity is to measure the percentage of body fat (the subject is obese when approximately >25% of body fat in men and approximately >30% of body fat in women).

In an example of use in medicine, a strain of the invention; or the cellular components, metabolites, secreted molecules, or any combination thereof of the invention; or a composition of the invention, is used in the treatment and/or the prevention of excess weight or obesity and, preferably, when caused by diet. As demonstrated in the present invention, administration of the *B. uniformis* CECT 7771 strain in animals with diet-induced obesity causes a reduction in weight gain (Example 3, Table 2). Overall, this means that the strain can be used for treating or preventing excess weight or obesity.

Given that the administration of the *B. uniformis* CECT 7771 strain produces a reduction in weight gain (Example 3, Table 2), said strain can also be used in cosmetic applications to reduce weight gain. Therefore, it is understood that a strain of the invention; or the cellular components, metabolites, secreted molecules or any combination thereof, of the invention; or a composition of the invention for reducing weight gain is also equivalent to a method for reducing weight gain (both for therapeutic and cosmetic purposes) comprising the administration of said strain, said components, metabolites or secreted molecules, or said composition to a subject.

Other alterations of lipid and glucose metabolism, wherein the immune system may also be affected, such as, but not limited to, diabetes mellitus type 2 and gestational diabetes, dyslipidemia (preferably hyperlipidemia and hypercholesterolemia), cardiovascular pathologies, hypertension, fatty liver (preferably non-alcoholic fatty liver or hepatic steatosis, nonalcoholic steatohepatitis, cirrhosis or hepatitis), metabolic syndrome, cancer, infections, etc. can occur in both normal-weight subjects and subjects with excess weight or obesity.

In another example of use in medicine, a strain of the invention; or the cellular components, metabolites, secreted molecules or any combination thereof, of the invention; or a composition of the invention, is used to decrease the growth and differentiation of adipose tissue in subjects with obesity or excess weight and at an earlier stage of excess weight or obesity, and, therefore relates to the use in the prevention and/or treatment of adipocyte hypertrophy. As demonstrated in example 3 and in FIG. 3, the strain object of the invention reduces the size of adipocytes, the increase (hypertrophy) of which at certain stages of life (particularly in childhood and adolescence) especially favors the development of excess weight and obesity in adulthood and other associated complications such as insulin resistance. In particular, administration of the CECT 7771 strain to obese animals gives rise to an increase in the number of small adipocytes (Example 3, FIG. 3).

In another example of use in medicine, a strain of the invention, or the cellular components, metabolites, secreted molecules or any combination thereof, of the invention; or a composition of the invention, is used in the treatment and/or prevention of hepatic steatosis or fatty liver. As demonstrated herein, administration of the *B. uniformis* CECT 7771 strain to both animal obesity models and control animals (non-obese) produces a reduction in the number of hepatocytes with high accumulation of fat (Example 3, FIG. 2). Overall, this means that the strain of the invention reduces fat accumulation in the liver.

The present invention also relates to the prevention and/or treatment of pathologies related to the aggravation of hepatic steatosis, such as, but not limited to, non-alcoholic hepatitis, steatohepatitis, fibrosis, cirrhosis, end stage liver disease or hepatocellular carcinoma. A strain of the species *B. uniformis* or the strain of the invention can be used for these or other pathologies accompanied by lipid accumulation in the liver and inflammation, which may be associated with obesity or excess weight or be a consequence of other alterations. These include, for example but not limited to, nutritional alterations (for example, but not limited to, malabsorption, protein-calorie malnutrition or parenteral nutrition); inherited or non-inherited metabolic alterations (for example, but not limited to, diabetes mellitus type 2, abetalipoproteinemia, or systemic carnitine deficiency); diseases caused by drug (for example, but not limited to, corticosteroids or ibuprofen) or toxic (for example, but not limited to, alcohol) exposure, chronic or acute hepatitis due to infection, cirrhosis, fibrosis, end stage liver disease; hepatic carcinoma or alterations of the pituitary gland. In particular, steatosis affects approximately 50% of patients with type 2 diabetes mellitus.

In another example of use in medicine, a strain of the invention, the cellular components, metabolites, secreted molecules or any combination thereof, of the invention; a composition of the invention, is used in the prevention and/or treatment of a disease caused by changes in blood lipid levels (for example, dyslipidemia) and preferably in blood triglyceride and/or cholesterol levels, due to which it is used to normalise said levels. Preferably the drug or nutritional composition is used to treat dyslipemia (synonymous with dyslipidemia). Preferably dyslipiedemia is hypertriglyceridemia and/or hypercholesterolemia. Dyslipidemia is a pathological condition whose only common element is an altered metabolism of lipids, with the consequent alteration of blood lipid and lipoprotein levels. Dyslipidemia may or may not be associated with obesity and the intake of high-fat diets and increased fat absorption. In turn, these changes are associated with an increased risk of cardiovascular disease, hypertension and diabetes, among other pathologies. The strain of the invention reduces the absorption of lipids and blood triglyceride and cholesterol levels, proving effective in the applications described, as demonstrated in Example 3, Table 2.

In another example of use in medicine, the strain of the invention; or the cellular components, metabolites, secreted molecules, or any combination thereof; or the composition of the invention, is used to reduce the amount of absorved lipids from the diet with respect to an untreated control. As shown in Example 3, the strain of the invention reduces the number of fat micelles that form chylomicra in intestinal enterocytes, i.e. it reduces the amount of dietary fat that is absorbed by more than 80% (Example 3, FIG. 4). Chylomicra are the way whereby dietary lipids are packaged and transported from the intestine to the lymphatic system and bloodstream to be used by the peripheral tissues, and the mechanism wherethrough the strain administered would limit its absorption and accumulation in the body. The absorption of dietary fat, in addition to leading to excess weight and/or obesity by causing an increase in accumulation in adipose tissue, may be the cause of other pathologies without causing obesity, such as, without limiting the scope of the invention, atherosclerosis, which is characterised by a thickening of the tunica intima of an artery with plaques where the fat is embedded, and dyslipidemia, characterised by alterations in the plasma concentrations of lipids (triglycerides and/or cholesterol and associated lipoproteins); pathologies associated with increased cardiovascular risk; or other alterations derived from the lipid-glucose metabolism ratio (for example, but not limited to, insulin resistance or diabetes).

In another example of use in medicine, a strain of the invention; or the cellular components, metabolites, secreted molecules, or any combination thereof, of the invention; or a composition of the invention, is used in the prevention and/or treatment of a cardiovascular disease. Cardiovascular diseases are those that affect the heart and blood vessels, including atherosclerosis, aneurysm, angina, stroke, cerebrovascular disease, congestive heart failure, coronary artery disease, acute myocardial infarction and peripheral vascular disease. Chronic inflammation and altered lipid metabolism (dyslipidemia) and glucose against which a *Bacteroides uniformis* strain, and preferably the strain of the invention, *B. uniformis* CECT 7771, is effective, dyslipidemia (hypercholesterolemia and hypertriglyceridemia), insulin resistance and diabetes, increased body fat or adipocyte hypertrophy, are risk factors for cardiovascular diseases and, therefore, their treatment and prevention may avoid the development of this other group of pathologies.

In another example of use in medicine, a strain of the invention; or the cellular components, metabolites, secreted molecules, or any combination thereof, of the invention; or a composition of the invention, is used in the prevention and/or treatment a disease caused by increased blood glucose levels, with respect to a control, and therefore is used to decrease the concentration of blood glucose levels (hyperglycemia) with respect to an untreated subject. This reduction in the concentration of glucose is produced in parallel with the reduction in insulin concentration and the reduction in the insulin resistance index, demonstrating that it improves insulin sensitivity and can therefore be used to treat or prevent metabolism alterations caused by insulin resistance and reduced insulin production.

The increase in blood glucose levels (hyperglycemia) can be diet-induced or arise from the development of insulin resistance (subjects who produce sufficient insulin but whose body fails to respond normally) or from the lack of insulin synthesis, with or without obesity, due to other metabolic alterations or drug interactions. Example 3 and Table 2 of the present invention provide experimental support to this preferred embodiment. The term "disease caused by increased blood glucose levels" relates to a health alteration caused by higher blood glucose levels than would be expected in a healthy individual with normal glucose levels, i.e. approximately 72-110 mg/dl or 4-7 mmol/l (fasting), or approximately <180 mg/dl (or 10 mmol/l) when measured 1.5 hours after meals. Said values are approximate average values, as the variation experienced and individual condition of each subject must be taken into account. The disease caused or associated with higher blood glucose levels is selected from the list comprising, but not limited to, neuropathy (nerve damage in limbs and/or organs); retinopathy (retinal damage in eyes), nephropathy (kidney damage that may cause renal failure), cardiovascular diseases (myocardial infarction); cerebrovascular disease (for example, cerebral thrombosis).

In another example of use in medicine, a strain of the invention; or the cellular components, metabolites, secreted molecules or any combination thereof, of the invention; or a composition of the invention, is used in the prevention and/or treatment of insulin resistance and/or diabetes (preferably gestational diabetes or type 2 diabetes mellitus). An example of more preferred use relates to the prevention and/or treatment of gestational diabetes or type 2 diabetes mellitus, a pathology associated, but not necessarily, with excess weight and/or obesity.

Type 2 diabetes mellitus is characterised by a relative deficit in insulin production and sensitivity in tissues and, thus, poor use of peripheral glucose. Type 2 diabetes mellitus accounts for 80%-90% of all diabetic patients. It often develops in adult life stages, and is very frequently associated with obesity. Several drugs and other causes can, however, cause this type of diabetes. For example, diabetes associated with prolonged use of steroids is very frequent, often associated with untreated hemochromatosis, and gestational diabetes not always associated with obesity.

In another example of use in medicine, a strain of the invention; or the cellular components, metabolites, secreted molecules or any combination thereof, of the invention; or a composition of the invention, is used in the prevention and/or treatment of metabolic syndrome. The term "metabolic syndrome" refers to the set of metabolic alterations that jointly increase the risk of diabetes and cardiovascular disease, including the combination of obesity, dyslipidemia (for example, triglycerides and hipecolesterolemia) and hyperglycaemia. As demonstrated in previous examples (Example 3, Table 2), the strain of the invention is useful in the simultaneous prevention and treatment of these alterations and, therefore, of metabolic syndrome.

In another example of use in medicine, a strain of the invention; or the cellular components, metabolites, secreted molecules or any combination thereof, of the invention; or a composition of the invention, is used in the prevention and/or treatment of hypertension. Hypertension is caused by changes in blood flow due to dysfunction of the inner layer of blood vessels. The factors that contribute to arterial hypertension include obesity, insulin resistance (insulin does not exert its vasodilator effect correctly), and dyslipidemia and chronic inflammation, which favour the deposition of lipids in the arteries and infiltration of inflammatory cells that cause vasoconstriction and, ultimately, atherosclerotic plaques. This invention demonstrates that a *Bacteroides uniformis* strain and preferably the strain of the invention, *B. uniformis* CECT7771, improves all these alterations and, therefore, may help prevent and treat the causes of hypertension.

In another example of use in medicine, a strain of the invention; or the cellular components, metabolites, secreted molecules or any combination thereof of the invention; or a composition of the invention, is used for improving the function of the immune system and, in particular, in the prevention and/or treatment of an inflammation-associated disease caused by an increased production of pro-inflammatory molecules and a reduction in anti-inflammatory molecules with respect to a control. In this regard, experimental data are shown in Example 4 and Table 3. Examples of pro-inflammatory proteins are, but not limited to, cytokines and chemokines and adipokines. Preferably, the pro-inflammatory proteins are selected from the list comprising, IL-1, IL-6, IL-8, IL-12, IL-16, C-reactive protein, TNF-α or MCP1 and leptin, or any combination thereof. More preferably, the pro-inflammatory proteins are selected from the list comprising TNF-α and leptin or any combination thereof. Examples of anti-inflammatory proteins that can reduce pro-inflammatory proteins include, but not limited to, IL-10 cytokine.

The term "disease associated with an increased production of pro-inflammatory proteins" relates to diseases caused by at least the production of a protein involved in inflammation (pro-inflammatory) of various types of tissues. Some of the diseases associated with increased production of pro-inflammatory proteins are also associated with excess weight and/or obesity, such as for example, but not limited to, type-2 diabetes, gestational diabetes, metabolic syndrome, fatty liver, non-alcoholic hepatitis, hypertension, dyslipemia, cardiovascular diseases, steatohepatitis or cancer. Other diseases associated with the increased production of pro-inflammatory proteins are not associated with excess weight and/or obesity, or may occur in the absence of obesity, such as for example, but not limited to, the aforementioned diseases (for example, diabetes) and others such as allergic inflammation.

In another example of use in medicine, a strain of the invention; or the cellular components, metabolites, secreted molecules or any combination thereof, of the invention; or a composition of the invention, is used to reduce inflammation of peripheral tissues, preferably of adipose and/or pancreatic tissue.

In another example of use in medicine, a strain of the invention; or the cellular components, metabolites, secreted molecules or any combination thereof, of the invention; or a composition of the invention, is used in the prevention and/or treatment of a disease associated with decreased innate and adaptive immune response, with respect to that of the control subjects.

The term "associated with decreased innate and adaptive immune response" relates to diseases or physiological situations characterised by immunosuppression of the function of the innate and adaptive immune system, which may lead to a higher susceptibility to develop certain pathologies such as infections. This disease associated with a decreased innate and adaptive immune response is preferably disease excess weight, obesity and associated disorders that involve an alteration of these immune functions. In this regard, experimental data are shown in Example 4 (FIGS. 5 and 6).

In another example of use in medicine, a strain of the invention; or the cellular components, metabolites, secreted molecules or any combination thereof, of the invention; or a composition of the invention, is used in the prevention and/or treatment of an infection or to enhance vaccination response and, therefore, the degree of protection of the subject against this antigen.

In another example of use in medicine, a strain of the invention; or the cellular components, metabolites, secreted molecules or any combination thereof, of the invention; or a composition of the invention, is used to restore the composition of the intestinal microbiota and, preferably, to reduce the concentration of potential pathogens such as enterobacteria in the intestinal contents of a subject, with respect to an untreated control. In an even more preferred example, the restoration of the composition of the intestinal microbiota, or a reduction in the concentration of enterobacteria in intestinal contents is carried out in a subject with excess weight, obesity or any disease associated therewith.

The restoration of the intestinal microbiota can be based, for example but not limited to, on the increase in the abundance of the genus *Bifidobacterium* and on the decrease in the abundance of bacteria of the Enterobaceriaceae family, whose concentrations are altered in obesity. This fact also implies a reduction in the risk of enterobacteria infections and a reduction in the pro-inflammatory signals that may be transmitted from the intestine to peripheral tissues (for example, liver) that may be affected in obese or non-obese subjects by various pathologies. As demonstrated in Example 4 and in FIG. 7, the administration of the strain object of the invention reduces the capacity of the microbiota (faeces) of obese animals to stimulate the synthesis of the inflammatory cytokine TNF-α in macrophages and dendritic cells. The inflammatory effect that causes alterations of the intestinal microbiota in obese subjects has been associated with insulin resistance, metabolic endotoxemia, hepatic steatosis, and alteration of the intestinal barrier function, which could be attenuated by the strain of the invention. Moreover, the strain of the invention also increases the number of *Bacteroides* spp. and *Bifidobacterium* spp in normal-weight subjects and can be used to increase or restore these microbial populations in the intestine, which may be altered due to conditions other than obesity and excess weight. Therefore, the CECT 7771 strain is additionally applicable to the prevention and treatment of diseases associated with alterations in the composition of the intestinal microbiota.

According to the present description, the strain of the invention; or the cellular components, metabolites, secreted molecules or any combination thereof, of the invention; or the composition of the invention, for use in the treatment and/or prevention of various diseases or metabolic alterations, for improving the function of the immune system or restoring the composition of the intestinal microbiota or reducing the concentration of enterobacteria, can obviously be understood as a method of treatment and/or prevention of such diseases or alterations, or a method for improving the immune function, or a method for restoring the composition of the intestinal microbiota, or a method for reducing the concentration of enterobacteria, which comprises administering a therapeutically effective amount of such a strain; or of said cell components, metabolites, secreted molecules, or any combination thereof, or of said composition, to a subject. Also, the present invention also covers the use of said strain, or of said cell components, metabolites, secreted molecules, or any combination thereof, for the manufacture of a nutritional composition, a pharmaceutical composition or a drug (as previously described), for the treatment and/or prevention of such diseases or metabolic alterations, for improving the function of the immune system or for restoring the composition of the intestinal microbiota or reducing the concentration of enterobacteria.

Another aspect of the present invention relates to a method of improving the bodily appearance of a subject, which comprises administering to said subject a strain of the invention; or the cellular component, metabolite, secreted molecule or any combination thereof of the invention; or a nutritional composition of the invention, for reducing body weight gain or contribute to weight loss, for cosmetic purposes. Within the scope of the present invention, it is understood that the subject to whom the strain of the invention or the cell component, metabolite, secreted molecule or any combination thereof of the invention; or the nutritional composition of the invention, is administered for cosmetic purposes is a healthy subject.

Throughout the description and claims the word "comprises" and its variants are not intended to exclude other technical features, additives, components or steps. For persons skilled in the art, other objects, advantages and features of the invention will become apparent partly from the description and partly from the practice of the invention. The following figures and examples are provided by way of illustration, and are not intended to be limiting of the present invention.

*uniformis* CECT 7771, HFD, high-fat diet, HFD+B, with a high-fat diet+*B. uniformis* CECT 7771. Results are expressed as means and standard deviations. Statistically significant differences were established applying the Mann-Whitney U Test (p<0.05).

Figure 5:
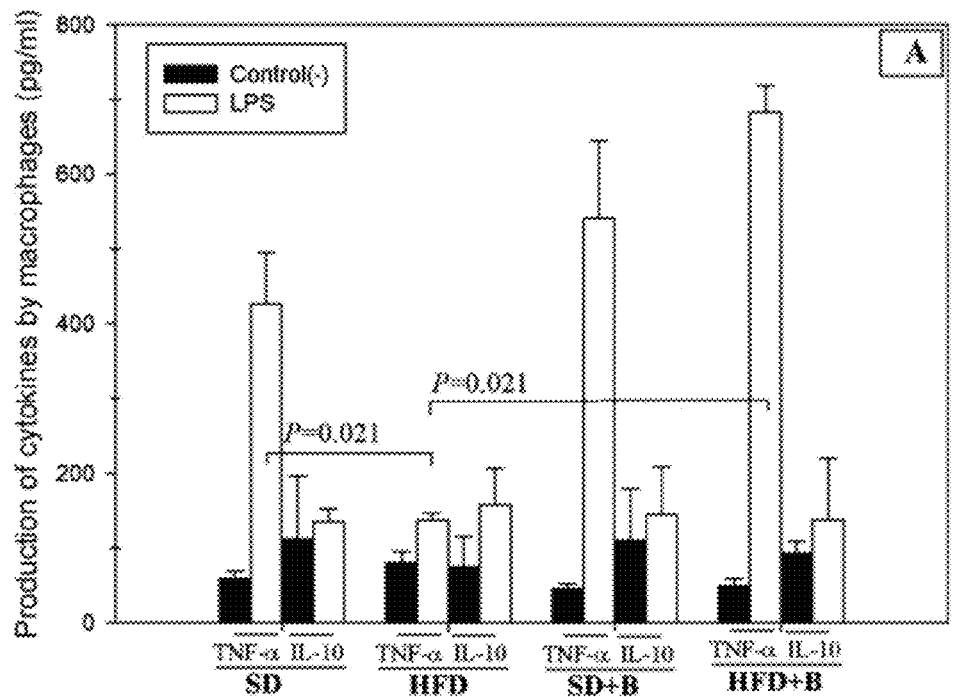
Figure 5:
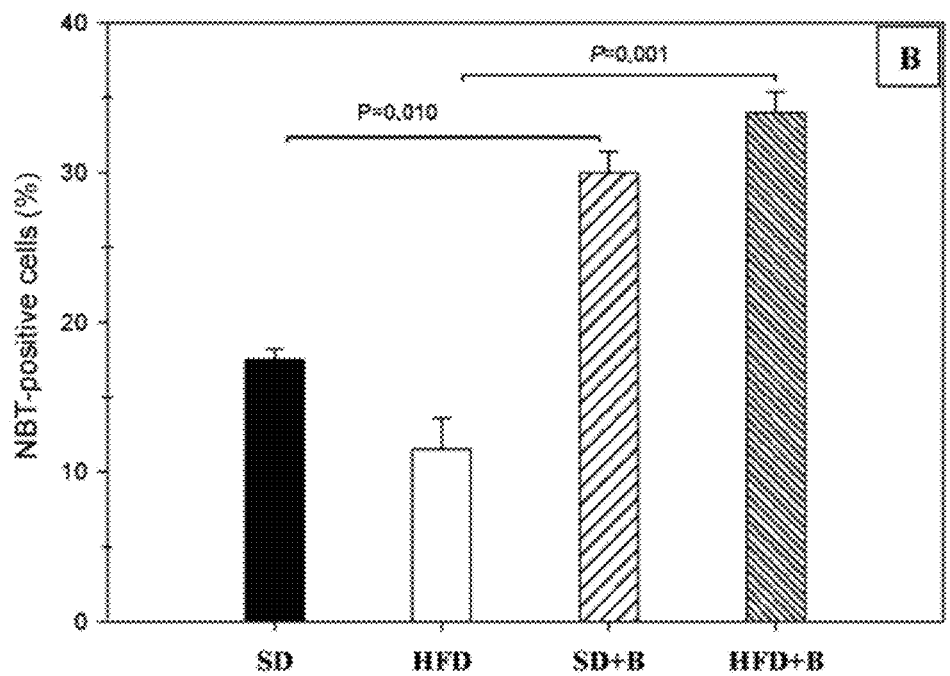

FIG. 5. Panel A shows the effect of administering the *B. uniformis* CECT 7771 strain ($5 \times 10^8$ cfu/day) to obese C57BL/6 mice (n=6/group) for 7 weeks on the role of macrophages stimulated with lipopolysaccharide (LPS) in the synthesis of inflammatory cytokines (TNF-α) and anti-inflammatory cytokines (IL-10). Panel B shows the effect of administering the strain in the respiratory burst in macrophage phagocytosis. SD, control animals with a standard diet, SD+B, control animals with a standard diet+*B. uniformis* CECT 7771, HFD, high-fat diet, HFD+B, with a high-fat diet+*B. uniformis* CECT 7771. Results are expressed as means and standard deviations. Statistically significant differences were established applying the Mann-Whitney U Test (p<0.05).

Figure 6:
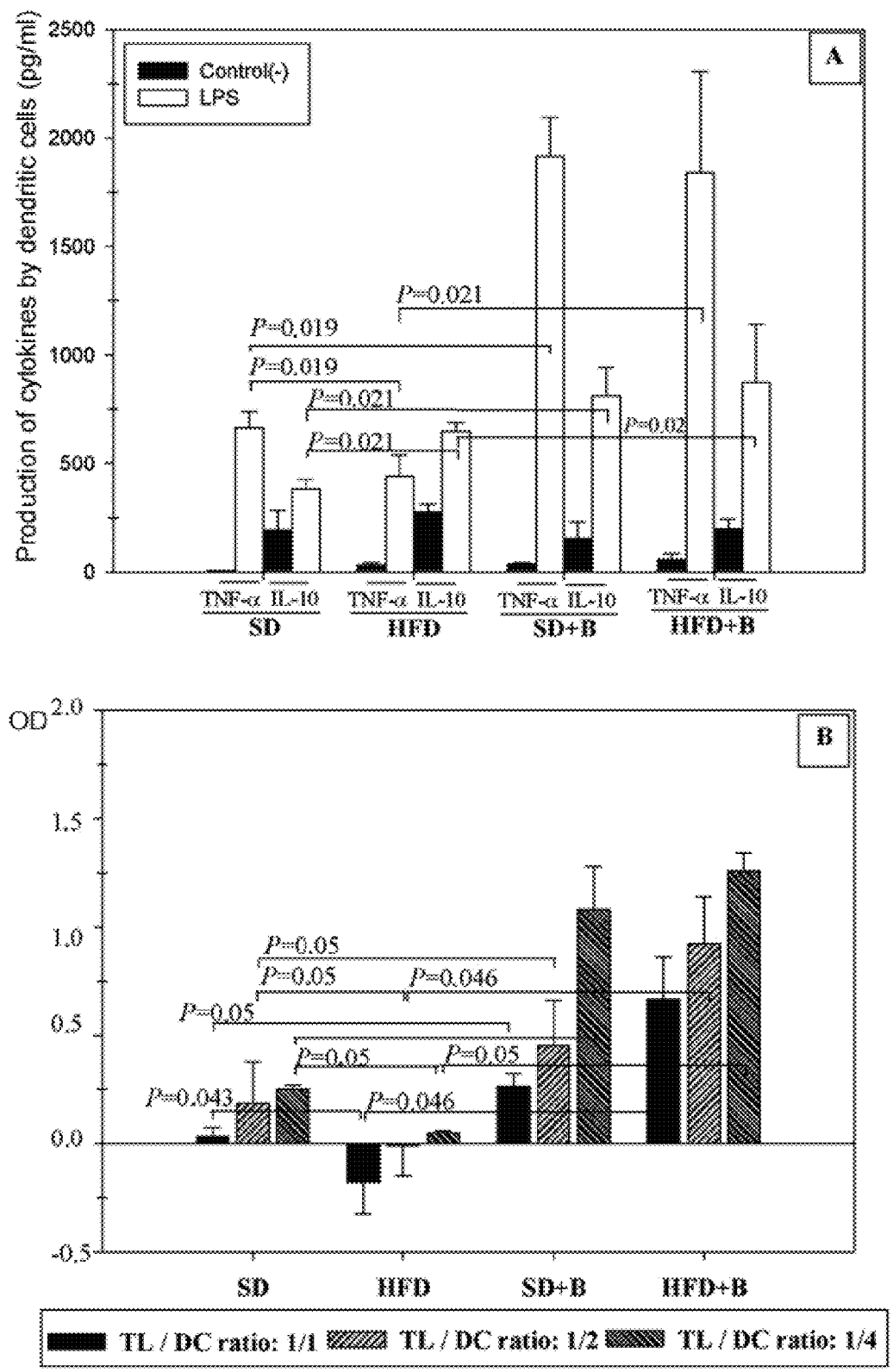

FIG. 6. A. Shows the effect of administering the *B. uniformis* CECT 7771 strain ($5 \times 10^8$ cfu/day) to obese C57BL/6 mice (n=6/group) for 7 weeks on the function of dendritic cells stimulated with lipopolysaccharide (LPS) in the synthesis of inflammatory cytokines (TNF-α) and anti-inflammatory cytokines (IL-10). B. Shows the effect of administration of the strain on the interaction between T cells and dendritic cells and their proliferation ability. CD4+ T lymphocytes (TL) were incubated with mature dendritic cells (DC) from different experimental groups of obese C57BL/6 mice (n=6/group) that were administered the strain ($10^8$ cfu/day) for 7 weeks. The cell ratio (TL/DC) in the mixture was 1:1, 1:2 and 1:4. SD, control animals with a standard diet, SD+B, control animals with a standard diet+*B. uniformis* CECT 7771, HFD, high-fat diet, HFD+B, with a high-fat diet+*B. uniformis* CECT 7771. Results are expressed as means and standard deviations. Statistically significant differences were established applying the Mann-Whitney U Test (p<0.05).

Figure 7:
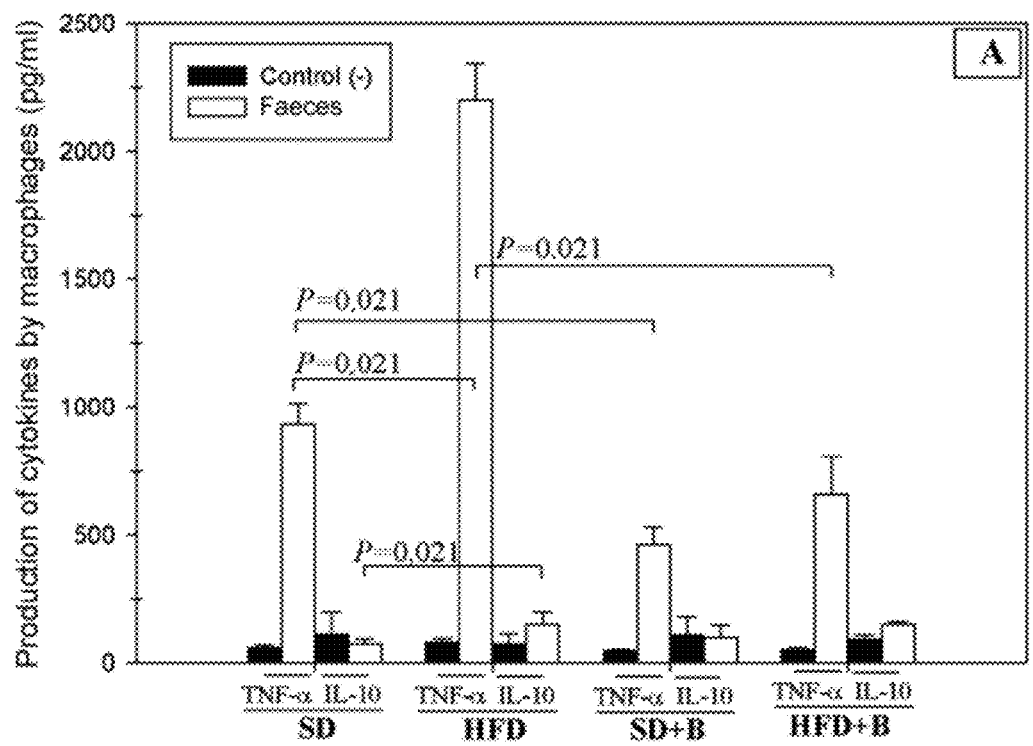
Figure 7:
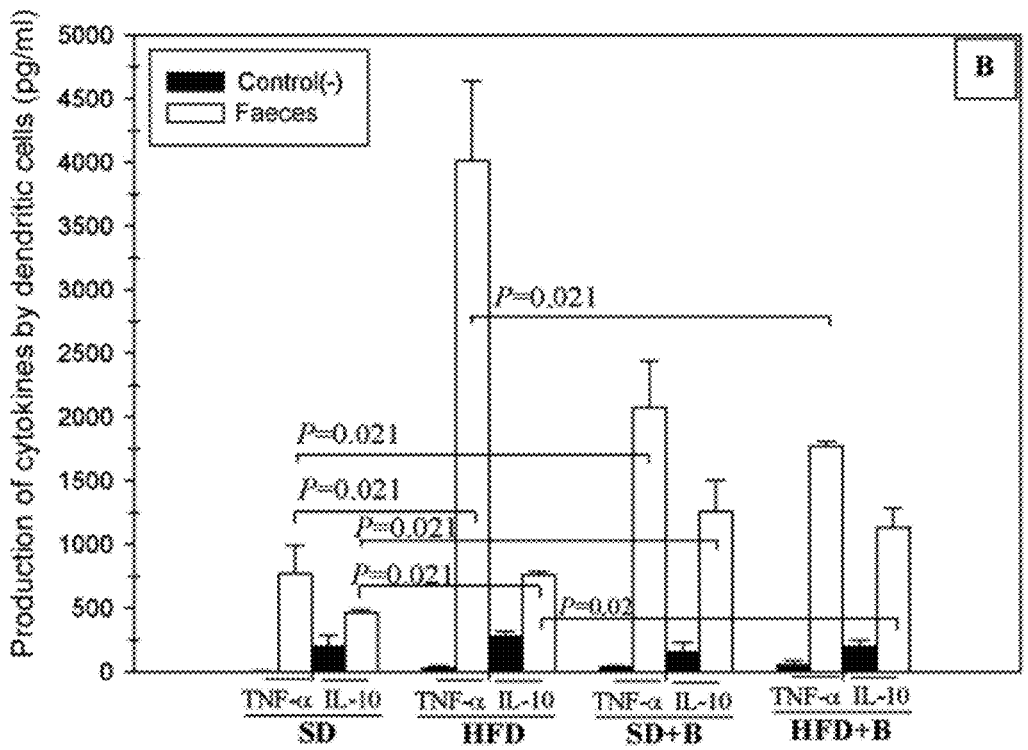

FIG. 7. A. Shows the effect of administering the *B. uniformis* CECT 7771 strain ($10^8$ cfu/day) to obese C57BL/6 mice (n=6/group) and controls for 7 weeks on the ability of intestinal microbiota (faeces) to stimulate the synthesis of inflammatory cytokines (TNF-α) and anti-inflammatory cytokines (IL-10) in macrophages (A) or dendritic cells (B) of control mice. SD, control animals with a standard diet, SD+B, control animals with a standard diet+*B. uniformis* CECT 7771, HFD, high-fat diet, HFD+B, with a high-fat diet+*B. uniformis* CECT 7771. Results are expressed as means and standard deviations. Statistically significant differences were established applying the Mann-Whitney U Test (p<0.05).

EXAMPLES

The invention is illustrated below by tests conducted by the inventors. The following specific examples provided herein serve to illustrate the nature of the present invention. These examples are included solely for illustrative purposes and must be interpreted as limitations to the invention claimed herein. Therefore, the described examples are not intended to limit the scope thereof.

Example 1

Isolation and Identification of the *B. uniformis* CECT 7771 Strain

We proceeded to the isolation of strains of the genus *Bacteroides* from faeces of healthy infants who had not been subjected to treatments with antibiotics for at least the month prior to sampling. The samples were kept at 4° C. and analysed within two hours after collection. Two grammes of each were diluted in 10 mM phosphate buffer containing a concentration of 130 mM NaCl (PBS) and homogenised in a Stomacher 400 Lab Blender (Seward Medical, London, UK) for 3 minutes and were diluted in peptone water. Aliquots of 0.1 ml of various decimal dilutions were inoculated onto Schaedler agar (Scharlau, Barcelona, Spain) supplemented with kanamycin (100 mg/L), vancomycin (7.5 mg/L) and vitamin K (0.5 mg/L), at 37° C. under anaerobic conditions. After incubation for 48 h at 37° C. under anaerobic conditions (AnaeroGen, Oxoid, UK), isolated colonies were selected and their morphology was confirmed under Gram staining. The identity of the isolates was confirmed by sequencing of the 16S ribosomal RNA gene from total DNA. The sequenced fragment was amplified using primers 27f (5"AGAGTTTGATCCTGGCTCAG-3': SEQ ID NO: 2) and 1401 r (5'-CGGTGTGTACAAGACCC-3': SEQ ID NO: 3) and purified using the GFX™ PCR commercial system (Amershan, Bioscience, UK). For the sequencing, primers 530F (5'-GTGCCAGCAGCCGCGG-3': SEQ ID NO: 4) and U-968f (5'-AACGCGAAGAACCT-TAC-3': SEQ ID NO: 5) were also used, in accordance with the procedures described by other authors (Gerhard et al., 2001. Appl. Environ. Microbiol., 67: 504-513; Satokari et al, 2001. Appl. Environ. Microbiol. 67, 504-513; Favier of ai, 2002. Appl. Environ. Microbiol, 68: 219-22). Sequencing was performed using an ABI 3700 {Applied Biosystem, Foster City, Calif.) automatic DNA sequencer.

Sequence 1,335 kb of the 16S ribosomal RNA gene of the CECT 7771 strain is SEQ ID NO: 1. The search for more closely related sequences was performed in the GenBank database using the BLAST (Altschul et al algorithm, J. Mol 1990 Biol, 215: 403-410) algorithm.

Upon comparing SEQ ID NO: 1 with the most similar sequences, an identity of 99% was obtained with respect to other strains of the species *B. uniformis* (GeneBank access no. AB0501). These results indicate that the strain of the present invention may very likely belong to said species.

The strain of the invention was molecularly typed using RAPD analysis using the M13 primer (5'-GAGGGTGGCG-GTTCT-3': SEQ ID NO: 6) and according to the previously described methodology (Antonie Van Leeuwenhoek, 2010, 98(1):85-92). The profiles of the randomly amplified DNA fragments showed that the strain object of the invention (β. *uniformis* CECT 7771) is different from other strains of the same species.

Example 2

Selection of the *B. uniformis* CECT 7771 Strain in Accordance with its Capability to Modulate, In Vitro, the Macrophage Response Related to Chronic Low-Grade Inflammation Associated with Obesity and According to the Ability to Modify Lipid Accumulation and Use of Glucose by Hepatocytes 2.1. Evaluation of the Effect of Bacterial Strains on Macrophages Bacterial strains and culture conditions. The following strains of the genus *Bacteroides* were used: *B. uniformis* CAY1 (CECT 7771), *B. uniformis* CBD2, *B. distasonis* CAY3, *B. fragilis* SX3, *B. fivegoldi* SX2, *B. dorei* SS1, *B. ovatus* SV2, *B. thetaiotaomicron* SAC4 and *B. caccae* SV3. The strains were inoculated into 10 ml of Brain Heart broth (BH; Schartau Chemie S. A., Barcelona, Spain) containing 0.05% cysteine (BH), at 1% with 24 hours of culture were incubated for 22 h at 37° C. in anaerobiosis. (AnaeroGen; Oxoid, Basingstoke, UK). The cells were collected by centrifugation (6,000 g, 15 minutes), washed twice in PBS (10 mM sodium phosphate, 130 mM sodium chloride, pH 7.4), and re-suspended in PBS containing 20% glycerol. Aliquots of these suspensions were frozen with liquid nitrogen and stored at −80° C. The number of viable cells after the freezing-thawing cycle was determined by counting on Schaedler Agar agar plates (Schartau, Barcelona, Spain) supplemented with kanamycin (100 mg/L), vancomycin (7.5 mg/L) and vitamin K (0.5 mg/L). Viability was over 90% in all cases. Each aliquot was used for a single assay. In order to evaluate the effects of dead bacteria, some of the aliquots were cold-activated (three freeze-thaw cycles −20° C.) and heat-inactivated (30 minutes at 80° C.). The pH values of the supernatants obtained were adjusted to 7.2 with NaOH and sterilised by filtration (0.22-μm pore size, Millipore, Bedford, Mass.) to eliminate the possible presence of viable cells. In order to evaluate the effects of other metabolites and compounds secreted into the culture medium, aliquots of the cell-free supernatants were conserved at −80° C. until use thereof. Likewise, the effect of incorporating probiotics into the culture medium by replacing part of the glucose of the BH medium with inulin (Inulin L-Light and Co LTD, Colnbrook, UK) was evaluated, its final concentrations being 0.5 g/l and 1.5 g/l, respectively. Under these conditions, the cells and supernatants were obtained from each strain and were used to perform the same macrophage and hepatocyte stimulation assays.

Macrophage culture and stimulation. Cells of the RAW 264.7 murine macrophage cell line were grown in Dulbecco's Modified Eagle Medium (DMEM, Sigma, USA), supplemented with 10% of fetal bovine serum (Gibco, Barcelona, Spain), streptomycin (100 μg/ml, Sigma) and penicillin (100 U/ml, Sigma). In order to conduct the stimulation experiments, cells were incubated at a concentration of $10^5$ ppm in Polystyrene Flat Bottom Plates with 24 Wells (Corning, Madrid, Spain) at 37° C., at 5% of $CO_2$. Suspensions of live and dead bacteria equivalent to $1×10^6$ colony-forming units (cfu)/ml and supernatant volumes of 30 μl were used as a stimulus. Lipopolysaccharide (LPS) purified from *Salmonella enterica* serotype *Typhimurium* (Sigma Chemical Co., Madrid, Spain) at a concentration of 1 μg/ml was used as a positive control. Cytokine production in non-stimulated cells was tested as a negative control. Each type of stimulus was tested in triplicate in two independent experiments. The culture supernatants were collected by centrifugation, fractioned and stored in aliquots at −20° C. until the detection of cytokines and chemokines.

Determination of cytokines and chemokines. The concentrations of cytokines (TNF-α and IL-10) of the supernatants of the macrophage cultures was measured using ELISA kits (BD Biosciences, San Diego, Calif.) following the company's instructions.

TABLE 1

Example the effect of stimulation with viable cells of different species and strains of the genus *Bacteroides* in the synthesis of pro-inflammatory and anti-inflammatory cytokines by macrophages.

| *Bacteroides* strains | Cytokine concentration | | |
|---|---|---|---|
| | TNF-α (pg/ml) | IL-10 (pg/ml) | TNF-α/IL-10 |
| DEMEN (control) | 491.2 (112.1)$^a$ | 97.2 (10.8)$^a$ | 5.00 (0.60)$^{a,b'}$ |
| LPS (1 mg/ml) | 1,425.4 (77.6)$^b$ | 162.3 (37.6)$^a$ | 9.04 (1.61)$^{b,a'}$ |
| B. dorei SS1 | 3,765.5 (150.0)$^{b,a'}$ | 215.8 (12.5)$^{b,b'}$ | 17.53 (1.71)$^{b,b'}$ |
| B. ovatus SV2 | 4,515.7 (211.3)$^{b,b'}$ | 271.5 (8.1)$^{b,b'}$ | 16.62 (0.28)$^{b,b'}$ |
| B. distasonis CAY3 | 4,462.4 (173.9)$^{b,b'}$ | 215.8 (9.7)$^{b,b'}$ | 20.74 (1.74)$^{b,b'}$ |
| <u>B.uniformis CECT 7771</u> | <u>2,998.4 (50.4)$^{b,a'}$</u> | <u>341.3 (13.5)$^{b,a'}$</u> | <u>9.91 (3.86)$^{b,a'}$</u> |
| B. uniformis CBD2 | 2,640.5 (80.2)$^{b,a'}$ | 105.4 (10.5)$^{a,b'}$ | 31.00 (16.55)$^{b,b'}$ |
| B. thetaiotaomicron SAC4 | 2,931.2 (464.5)$^{b,a'}$ | 109.2 (3.0)$^{a,b'}$ | 26.95 (5.01)$^{b,b'}$ |
| B. fragilis SX3 | 6,657.3 (278.3)$^{b,b'}$ | 81.2 (14.6)$^{a,a',b''}$ | 219.17 (41.39)$^{b,b'}$ |
| B. caccae SV3 | 11,622.0 (818.3)$^{b,b'}$ | 171.7 (12.9)$^{b,b'}$ | 67.69 (0.32)$^{b,b'}$ |
| B. finegoldii SX2 | 6,535.8 (62.2)$^{b,b'}$ | 83.5 (17.4)$^{a,b'}$ | 80.75 (16.07)$^{b,b'}$ |

*Results are expressed as means and their standard deviation (sd, values n parentheses). Statistically significant differences were established applying Tukey's Test at a value of $P < 0.050$. Different letters in the same column indicate significant differences between the means in relation to the control value (a-b) or to the value of the cells stimulated with *B. uniformis* CECT 7771 (a'-b'). The data corresponding to the strain of the invention are underlined.

The strain object of the invention is selected from among others of the same genus due to being one of the strains that induced the lowest concentrations of pro-inflammatory molecules (TNF-α) involved in the state of chronic inflammation associated with obesity that causes resistance to the effects of insulin and leptin (Table 1). The strain of the invention was also selected for inducing the synthesis of the highest concentration of the anti-inflammatory and regulatory IL-10 cytokine by macrophages, which can help reduce inflammation in the context of obesity (Table 1). Other strains of the same species as *B. uniformis* CBD2 induced a significantly higher proportion of the TNF-α/IL-10 factor object by the patent (CECT 7771), indicating that the pro-inflammatory/anti-inflammatory cytokine balance induced by the latter is more favorable than that induced by the other strains. The immunological properties of the selected bacteria are not common to all the intestinal bacteria of the same genus (*Bacteroides*) or species (β. *uniformis*) and, therefore, make it particularly suitable for use in the treatment and prevention of excess weight, obesity and metabolic alterations, associated or not, and related to inflammation.

2.2. Evaluation of the Effect of the Bacterial Strains in Hepatocytes

Bacterial strains and culture conditions. The following strains of the genus *Bacteroides* are used: *B. uniformis* CAY1 (CECT 7771), *B. uniformis* CBD2, *B. distasonis* CAY3, *B. fragilis* SX3, *B. fivegoldi* SX2, *B. dorei* SS1 and *B. ovatus* SV2. The strains were grown in BH broth containing 0.05% cysteine and the cell suspensions and culture supernatants were collected and stored until use as indicated in section 2.1.

Cultivation of HepG2 cells. Cultures of liver-derived human cells belonging to the HepG2 cell line, widely used as a hepatic model, were used. The cells were cultivated in DMEM supplemented with fetal calf serum (10%, v/v) (FBS), penicillin (100 units/nil) and streptomycin (100 μg ml). Cultures were maintained (37° C.) in a humidified 5% $CO_2$ atmosphere with medium change every 48 h until reaching 70-80% of convergence, at which time they were used for the studies. Prior to its addition to the cell culture, a mixture of oleic acid (18: 1TO9, Sigma-Aldrich) (AO) was prepared and albumin (BSA) (A2153, Sigma-Aldrich), under aseptic conditions. An aliquot (5 g) of BSA dissolved in Dulbecco's modified medium (protein-free) (DMEM), used for cell culture, tempered to 40° C. The pattern of oleic acid was added to this solution, drop-wise and under constant stirring, a final concentration of 0.8 M. Based on the convergence cultures, in order to carry out and standardise the results of the various studies, the cells were re-suspended in DMEM and seeded in multiple-well plates (×24) at a density of $1 \times 10^8$ cells/well. The cells were incubated (37° C./5% C02) under these conditions for 24 hours. After this period, the cultures were washed (×2) with buffered saline solution (PBS) and 1 ml of DMEM (not supplemented with FBS) was added, at a concentration of 2 mM of the AO/BSA mixture in the presence or absence of cell suspensions ($10^8$ colony-forming units/nil) of the different bacterial strains indicated in the preceding section. The cultures were returned to the incubator for an additional 24 hours. Control cultures incubated with DMEM (not supplemented with FCS) but without AO cultures were included in all the studies.

Effect of various species and strains of Bacteroides in the accumulation of triglycerides and cholesterol in HepG2 cultures. The quantification of the total concentration (nmol/L) of triglycerides (TG) and cholesterol (CHOL) in HepG2 cultures exposed (24 hours) to the AO/BSA mixture (2 mM in DMEM) in the presence or not of the cell suspensions of the different bacterial strains described was carried out using commercial enzymatic kits (Triglycerides and Cholesterol Liquid, Quimica Analitica Aplicada, S.A., Spain). Quantification of TG and CHOL was conducted in cell homogenates with a solution (300 μl) of PBS (pH 7)/0.1% Triton-X100, using the pattern provided in the corresponding commercial kit.

Figure 1:
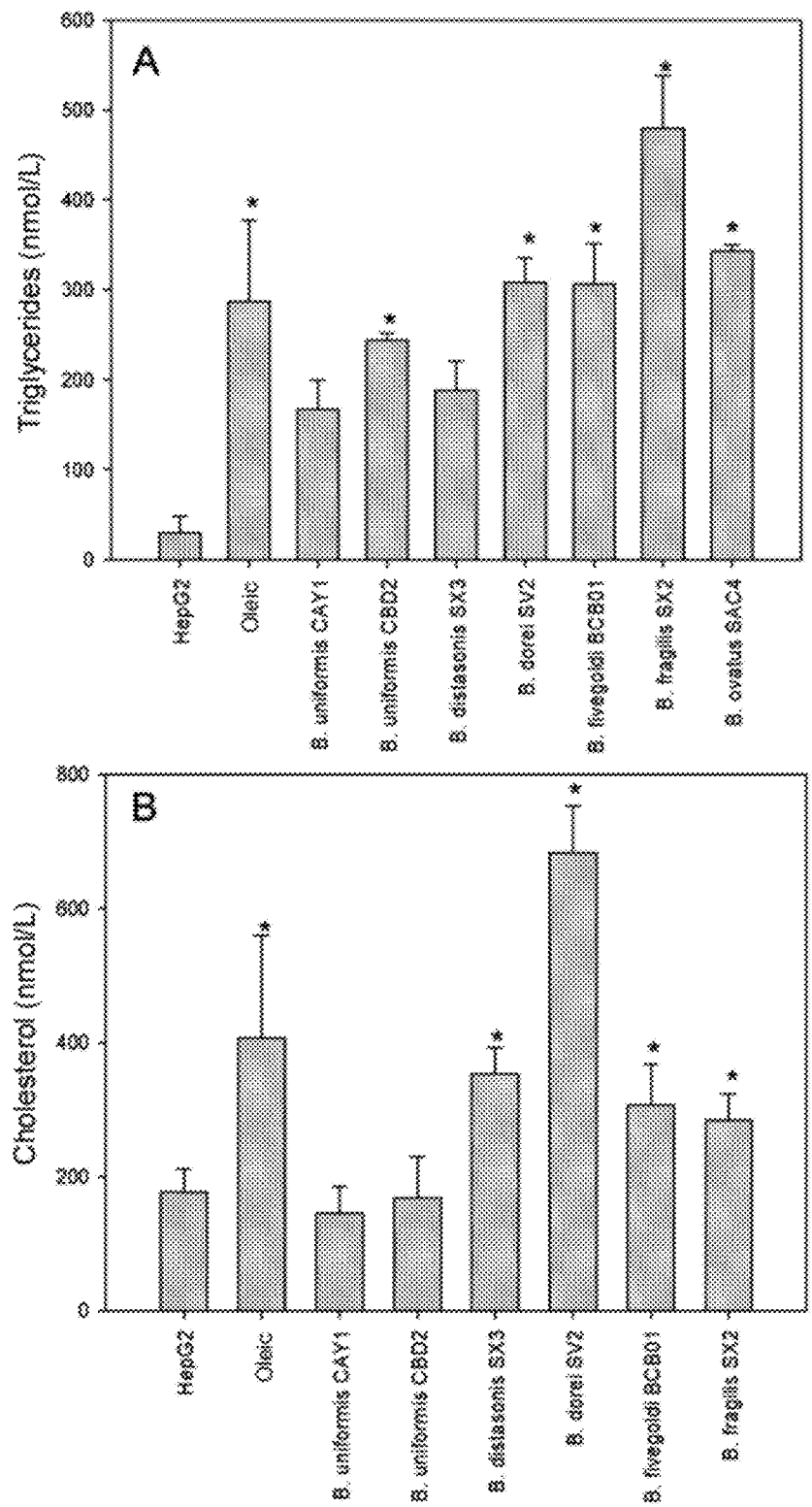
FIG. 1 shows the differential effect of strains of different species of the genus *Bacteroides* and of the species *B. Uniformis* on the accumulation of triglycerides (A) and cholesterol (B) in the hepatocytes and in the use of glucose (C). Results are expressed as means and their standard deviation. *Statistically significant differences with respect to the *B. uniformis* CECT 7771 strain (equivalent to CAY1) applying ANOVA and Tukey's Test ($p<0.05$).
Figure 1:
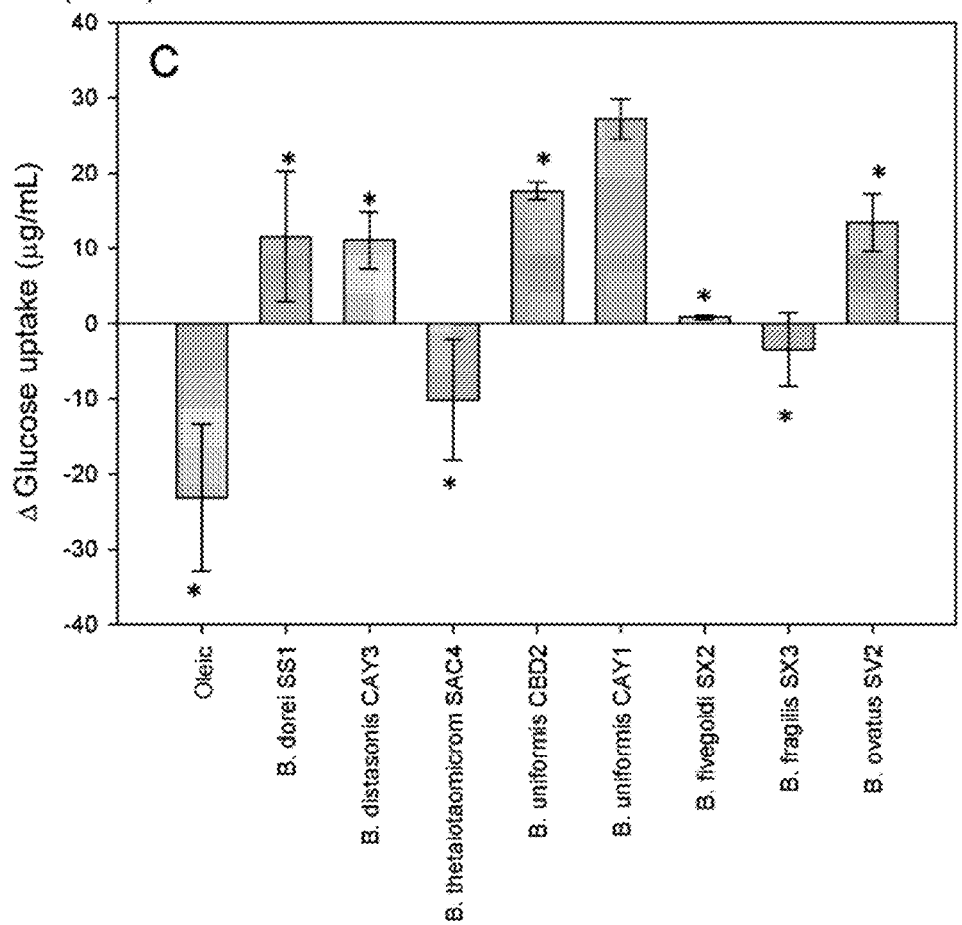

The strain object of the invention was selected from among others of the same genus and of the same species for their ability to reduce triglyceride and cholesterol accumulation in hepatocytes (FIG. 1). The B. uniformis CECT 7771 strain reduced the accumulation of triglycerides in comparison with other strains of different species such as B. dorei, B. fivegoldi, B. fragilis and B. ovatus and of the same species such as B. uniformis CBD2 (FIG. 1A). The B. uniformis CECT 7771 strain also reduced the accumulation of cholesterol in comparison with other strains of different species such as B. distasonis, B. dorei, B. fivegoldi, B. fragilis and B. ovatus (FIG. 1B).

Effect of Various Species and Strains of Bacteroides on Glucose Use and Insulin Resistance The influence of different bacterial strains on insulin resistance induced by treatment with oleic acid was evaluated by incubating (4 hours) HepG2 cultures exposed for 24 hours to 2 mM of AO/BSA in DMEM with a glucose solution (100 μg/mL) supplemented with insulin (10 ng/mL) in the presence or absence of different bacterial suspensions. The potential uptake of glucose by the bacteria was considered by incubating these means without addition to cell cultures. The influence of the bacterial suspensions on insulin resistance was evaluated by quantifying glucose uptake and intracellular concentration thereof in hepatocytes using a commercial enzymatic kit (Glucose Liquid, Quimica Analitica Aplicada, S.A., Spain). In FIG. 1C it can be observed that hepatocytes exposed to oleic acid have a reduced ability to use glucose even in the presence of insulin with respect to the controls. However, the strain of the invention (β. uniformis CECT 7771) improved the ability of hepatocytes to use glucose and, thus, their insulin sensitivity to a greater degree than other strains of the same genus and species, due to which it was considered the best candidate for the applications object of the patent.

Example 3

Effect of Administration of the B. uniformis CECT 7771 Strain on Biometric and Biochemical Parameters, Absorption of Lipids in the Intestine and Histology of Adipose Tissue and Liver 3.1. Animal Model of Obesity and Sampling.

Adult male C57BL-6 mice (6-8 weeks; Harlan Laboratorios) were used. The animals were kept under controlled temperature (23° C.), with a 12 hour light/dark cycle in an atmosphere with 40%-50% relative humidity.

Obesity was induced by feeding the mice a high-fat diet (HFD) which provided 60% of energy in the form of lipids (60/Fat, Harlan Laboratorios) at the expense of a reduction in carbohydrates, for 7 weeks, while the non-obese mice were fed a conventional diet that provided 12.4% of energy as lipids. The mice had free access to water and diet. Weight was monitored weekly. The experiments were conducted in accordance with the rules of the Animal Ethics Committee.

The animals were randomly divided into four groups (n=6/group): (1) controls that were fed a standard diet (SD), controls that were administered the strain of the invention (SD+strain), obese mice on being fed a high-fat diet (HFD) and obese mice that were administered the strain CECT 7771 (HFD+strain). The strain was administered at a daily dose of 5×10 8 cfu/day by intragastric catheter orally for 7 weeks. The bacterium is administered in the form of a nutritional composition comprising 10% skimmed milk supplemented with the bacteria at the indicated concentration of $5 \times 10^8$ cfu per each 100 μl of composition. The nutritional composition was administered to the SD-fed control groups and HFD-fed obese mice without the bacteria as a placebo. After the treatment periods, the animals were anaesthetised and sacrificed by cervical dislocation and samples of adipose (epididymal) and hepatic tissue and blood was drawn by cardiac puncture for analysis as described below.

3.2. Effects on the Liver and Adipose Tissue.

Samples of adipose (epididymal) and hepatic tissue were washed with saline solution and fixed in 10% buffered formalin, embedded in paraffin, cut into 4-5 μm sections and stained with hematoxylin eosin. The severity of the steatosis (lipid accumulation in the liver) was determined by analysing ten fields of each section set with bright-field microscope (Olympus), according to the following scale: grade 1 (no steatosis); grade 2, when hepatocyte fat occupied less than 33% of the cell; grade 3, when hepatocyte fat occupied between 34%66% of the cell; grade 4, when hepatocyte fat occupied over 66% of the cell. Adipocyte size was measured by image analysis using NIS-Elements BR 2.3 software, evaluating at least 100 cells per experimental group and tissue type.

Figure 3:
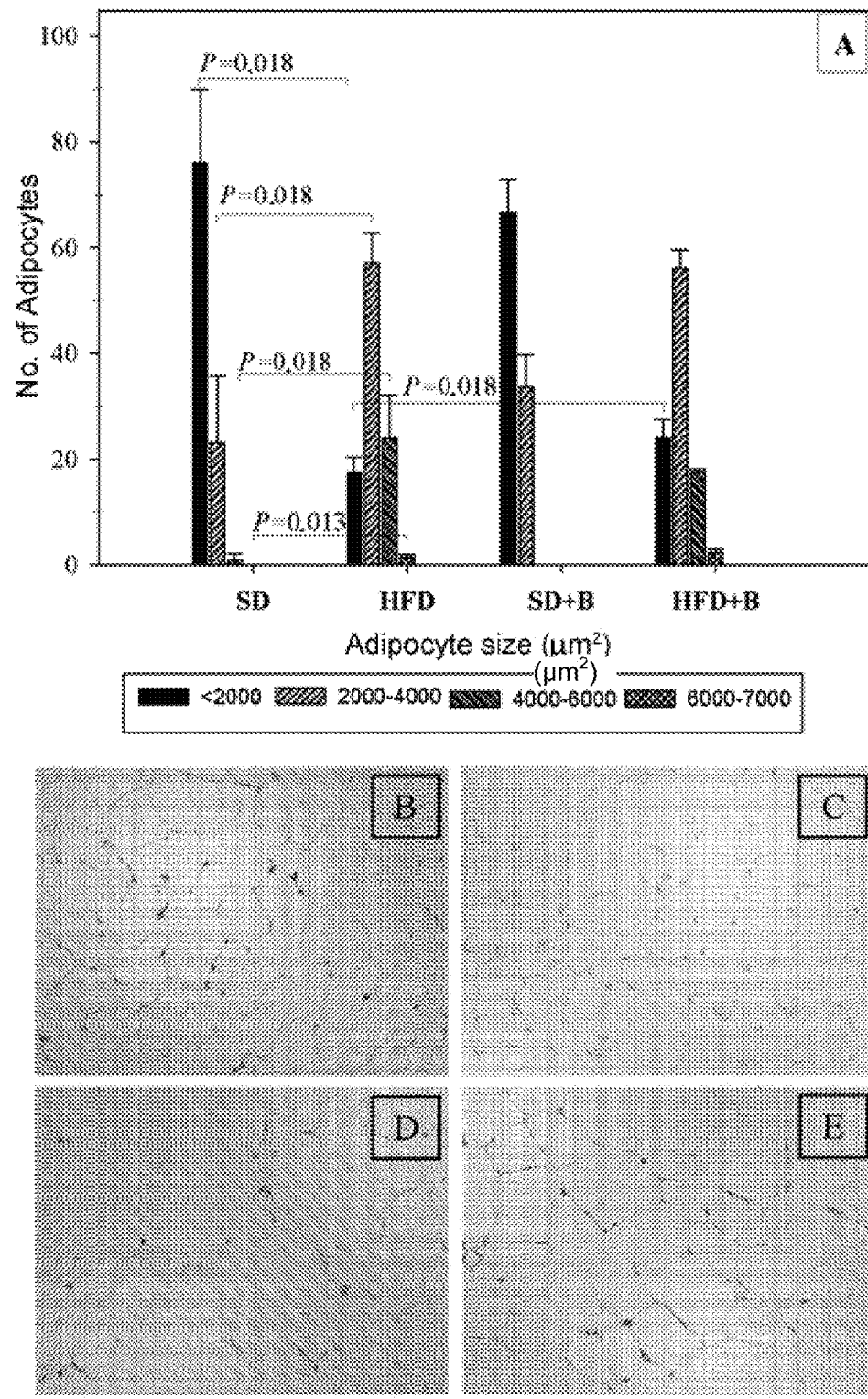
FIG. 3 shows the effect of administering the *B. uniformis* CECT 7771 strain ($5 \times 10^8$ cfu/day) to obese C57BL/6 mice (n=6/group) for 7 weeks on adipocyte development, classified by size intervals. Panel A: SD, control animals with a standard diet, SD+B, control animals with a standard diet+*B. uniformis* CECT 7771, HFD, high-fat diet, HFD+B, with a high-fat diet+*B. uniformis* CECT 7771. Results are expressed as means and standard deviations and the statistically significant differences were established applying the Mann-Whitney U Test ($p<0.05$). Panels B-E. The size of the adipocytes in a histology section of epididymal tissue stained with hematoxylin and eosin is shown. Panel B: SD; Panel C: SD+*B. uniformis* CECT 7771; Panel D: HFD; Panel E: HFD+β. *uniformis* CECT 7771.

The results indicate that the strain object of the invention reduces the size of adipocytes in epididymal tissue, whose increase (hypertrophy) at certain stages of life (childhood and adolescence) favors the development of excess weight and obesity in adulthood is associated with a positive imbalance between energy intake and energy expenditure (Macia et al., 2006. Genes Nutr., 1: 189-212). By contrast, the reduction in adipocyte size is related to the decreased resistance to insulin and glucose concentrations (Varady et al., 2009. Metabolism 58: 1096-101). In particular, administration of the CECT 7771 strain to obese animals gives rise to an increase in small adipocytes (<2000 µm$^2$), while in obese animals which have not been administered the strain recorded an increase in all large adipocytes (2000-7000 µm$^2$) and a reduction in small adipocytes (<2000 µm$^2$) (Example 3, FIG. 3). Histology sections of adipose tissue also show these effects.

The increased size of the adipocytes is also related to the increase in the uptake of fatty acids by the liver, giving rise to hepatic steatosis and complications, so that the strain can also help to avoid or ameliorate these alterations. Therefore, the B. uniformis CECT 7771 strain reduces the size of adipocytes, i.e. it is useful in the treatment of alterations in the development of this type of cells leading to hypertrophy thereof which, maintained over time, can lead to excess weight and obesity, in addition to other diseases not necessarily associated with obesity.

Figure 2:
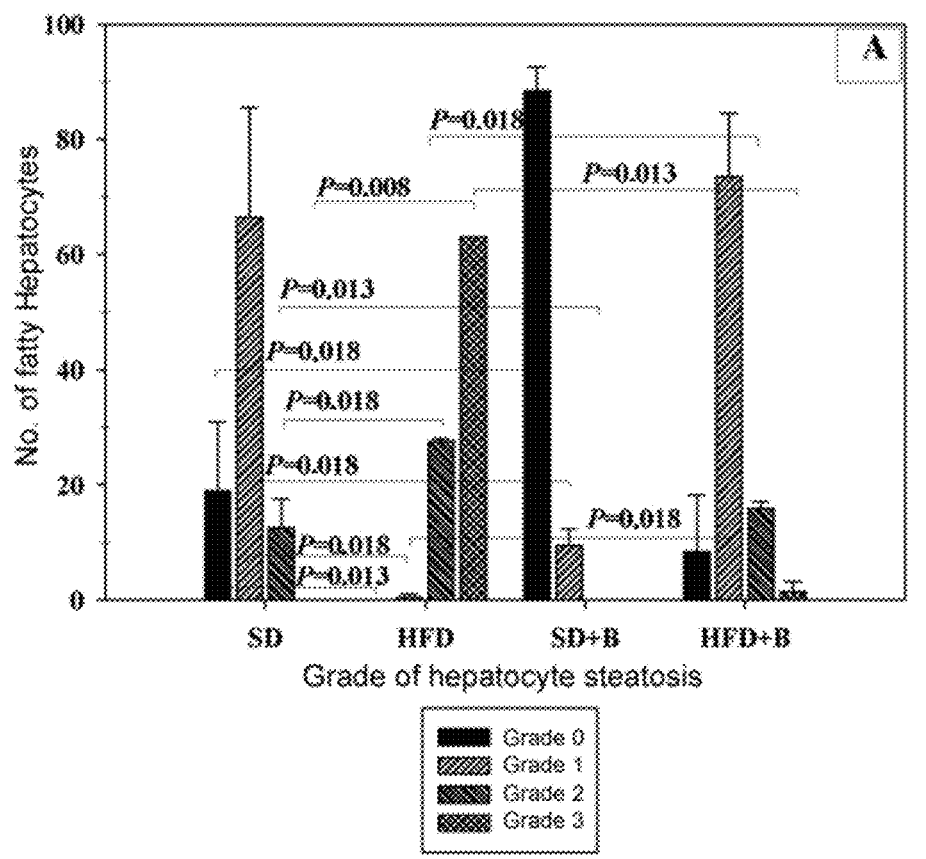
FIG. 2 shows the effect of administering the *B. uniformis* CECT 7771 strain ($5 \times 10^8$ cfu/day) to obese C57BL/6 mice (n=6/group) for 7 weeks on the development of steatosis (accumulation of lipids in the liver). Panel A: SD, control animals with a standard diet; SD+B, control animals with a standard diet+*B. uniformis* CECT 7771; HFD, high-fat diet, HFD+B, with a high-fat diet+*B. uniformis* CECT 7771. Results are expressed as means and standard deviations and the statistically significant differences were established applying the Mann-Whitney U Test ($p<0.05$). Panels B-E. The number of fatty hepatocytes in a histology section of liver tissue stained with hematoxylin and eosin, in accordance with the degree of accumulation of fat in the cell, is shown in ascending order (0-3). Panel B: SD; Panel C: SD+*B. uniformis* CECT 7771; Panel D: HFD; Panel E: HFD+β. *uniformis* CECT 7771.
Figure 2:
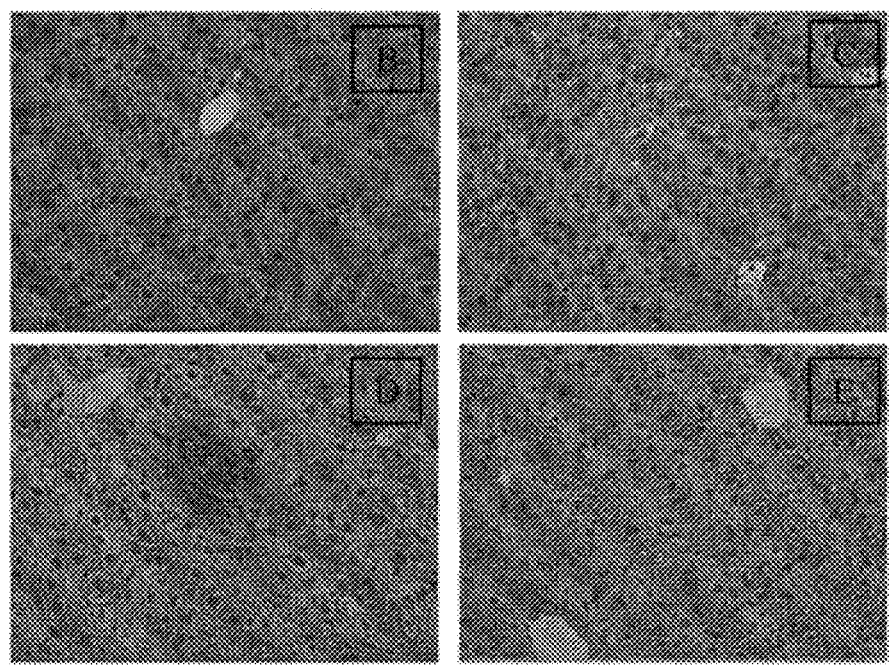

The strain of the invention reduces the accumulation of fat in the liver (steatosis) associated with the intake of high-fat diets, obesity and various diseases such as non-alcoholic hepatitis (Musso et al., 2010. Hepatology 52: 79-104). Specifically, the strain produces a decrease in the number of grade 2 and 3 hepatocytes, with maximum fat content, and an increase in the number of grade 0 and 1 hepatocytes, with lower fat content; however, in obese animals that were not administered the strain, proportion of hepatocyte type is reversed, predominating those with maximum fat content. In control animals, the administration of the strain produces an increase in grade 0 hepatocytes (lean) and a reduction in the number of grade 1 and 2 hepatocytes. (Example 3, FIG. 2). Thus it is demonstrated that administration of the strain reduces overall fat accumulation in the liver, diet-induced or otherwise.

3.3. Effects on Biometric and Biochemical Parameters.

Total body weight was monitored weekly and final weight gain was determined with respect to initial weight. Additionally, the weight of adipose tissue (epididymal and perirenal) per 100 g body weight was estimated after sacrifice. The glucose, triglyceride and cholesterol levels were determined in serum samples obtained from peripheral blood after sacrifice using colorimetric methods (Quimica Clinica Aplicada, S.A., Amposta, Spain) and insulin samples obtained using ELISA (BD Bioscience, San Diego, Calif., USA). Furthermore, the cholesterol and triglyceride levels were determined in the lipids extracted from the liver after sacrifice using the same methodology. In order to evaluate the postprandial glycemic response, at 6 weeks of treatment and after fasting for 4 hours, the mice were also administered an oral dose of glucose (2 g/kg) and blood samples were taken at different times (15, 30, 60, 90 and 120 min), whereupon the changes in glucose concentration was determined using test strips (Glucosa strips; Ascensia Esyfill, Bayer, Tarrytown, N.Y., USA) and a glucometer (Ascensia VIGOR, Bayer Tarrytown, N.Y., USA).

As shown in Table 2, administration of the strain of the patent, B. uniformis CECT 7771, to obese animals reduces their weight gain significantly after 7 weeks of intervention, indicating that it is effective in the prevention and treatment of excess weight and obesity.

TABLE 2

Biometric and metabolic parameters in mice fed a high-fat or standard diet, supplemented or not with the B. uniformis CECT 7771 strain.

| | Experimental Groups | | | | | | | |
|---|---|---|---|---|---|---|---|---|
| | SD | | HFD | | SD + B | | HFD + B | |
| Parameter | Mean | sd | Mean | sd | Mean | sd | Mean | sd |
| Biometric parameters | | | | | | | | |
| Weight gain (%) | 24.21 | 3.34 | 36.19 | 1.55 | 23.61 | 3.17 | 30.33 | 0.92 |
| Adipose tissue (g)/100 g Body weight | 0.06 | 0.04 | 0.15 | 0.03 | 0.03 | 0.02 | 0.14 | 0.04 |
| Serum parameters | | | | | | | | |
| Cholesterol (mg/dl) | 120.00 | 13.67 | 176.02 | 14.91 | 128.22 | 11.91 | 143.97 | 17.29 |
| Tryglicerides (mg/dl) | 130.31 | 11.56 | 156.99 | 27.47 | 129.77 | 13.94 | 118.21 | 10.04 |
| Glucose (mg/dl) | 219.81 | 26.41 | 229.47 | 13.83 | 372.41 | 13.50 | 233.52 | 30.62 |
| Insulin (µg/l) | 0.57 | 0.47 | 1.59 | 0.09 | 0.69 | 0.05 | 0.92 | 0.14 |
| Leptin (ng/ml) | 8.07 | 1.12 | 18.28 | 4.28 | 6.80 | 1.23 | 12.98 | 3.24 |
| Hepatic lipids | | | | | | | | |
| Cholesterol (mg/g) | 29.94 | 4.08 | 35.51 | 4.35 | 29.22 | 6.32 | 27.48 | 6.39 |
| Tryglicerides (mg/g) | 22.93 | 13.03 | 45.99 | 11.53 | 31.36 | 4.76 | 34.17 | 9.51 |

| | Análisis estadístico | | |
|---|---|---|---|
| Parameter | Value P HFD vs SD | Value P SD + B vs SD | Value P HFD + B vs HFD |
| Biometric parameters | | | |
| Weight gain (%) | 0.007* | 0.890 | 0.005* |
| Adipose tissue (g)/100 g body weight | 0.016* | 0.150 | 0.423 |

TABLE 2-continued

Biometric and metabolic parameters in mice fed a high-fat or standard diet, supplemented or not with the *B. uniformis* CECT 7771 strain.

| Serum parameters | | | |
|---|---|---|---|
| Cholesterol (mg/dl) | <0.001* | 0.222 | 0.003* |
| Tryglicerides (mg/dl) | 0.041* | 0.937 | 0.004* |
| Glucose (mg/dl) | 0.001* | 0.584 | 0.002* |
| Insulin (μg/l) | 0.018* | 0.892 | 0.018* |
| Leptin (ng/ml) | <0.001* | 0.048* | 0.014* |
| Hepatic lipids | | | |
| Cholesterol (mg/g) | 0.029* | 0.801 | 0.024* |
| Tryglicerides (mg/g) | <0.001* | 0.142 | 0.039* |

SD: standard diet group (control) (n = 6)
SD + B: group with DS and supplemented orally with 5.0 × 10$^8$ CFU/day of *B uniformis* CECT 7771 (n = 6),
HFD: group with high-fat diet (n = 6), HFD + B:
HFD group and supplemented orally with 5.0 × 10$^8$ CFU/day of *B uniformis* for 7 weeks (n = 6). The biochemical parameters were determined in plasma after the intervention.
$^a$Total weight gain was calculated at the end of the intervention and expressed in relative values with respect to the initial weight of each mouse.
$^b$The relative weight of adipose tissue, including epididymal and perirenal tissue, per each 100 g of body weight was calculated after the intervention. The values of all the parameters are expressed as means and their standard deviations.
*The statistical analysis was performed applying ANOVA and, subsequently, Tukey's Test for normally distributed data or the Mann-Whitney U Test for those without normal distribution. Significant differences were established at a value of P < 0.050.

As shown in Table 2, the strain of the invention administered in vivo also regulates glucose metabolism, reducing its concentration in peripheral blood in obese animals; for example, high levels of serum glucose 485.9 mg/dl detected in obese mice tend to become normalised after administering the strain object of the invention, achieving significantly lower levels of 233.5 mg/dl (P=0.002), in proportion to the reduction of insulin levels (1.593 versus 0.920 μg/l; P=0.018). The increase in plasma glucose concentration is indicative of an alteration in their metabolism and in insulin synthesis or response and can be positively regulated by the strain object of the invention, reducing the risk of developing insulin resistance and diabetes and enhancing treatment. Furthermore, the HOMA (Homeostasis Model Assessment) index was determined, which enables the estimation of insulin resistance (a high index indicates low insulin sensitivity) sensitivity) and the function of pancreatic beta cells. This index was estimated based on fasting glucose and insulin levels using the following equation HOMA=Insulin (μg/l)×Glucose (mg/dl)/405. The HOMA index in obese subjects was 1, 91 1, while in obese subjects treated with the strain it was 0.530, thereby detecting a significant reduction that indicates the positive effect of the strain on improving insulin sensitivity. Moreover, the strain of the invention reduces postprandial glycemic response after an oral dose of glucose, reducing the area under the glucose curve in obese subjects, which also indicates an improvement in glucose metabolism and insulin sensitivity. As shown in Table 2, the strain object of the invention also reduces the hyperleptinemia characteristic of diet-induced obesity, indicating an improvement in its function in the regulation of lipid and glucose metabolism.

The strain of the invention administered in vivo regulates lipid metabolism, reducing, in particular, the concentration of triglycerides and cholesterol in peripheral blood in obese animals. Thus, the elevated serum triglyceride levels detected in obese mice were significantly reduced upon administering the strain object of the invention from 156.99 to 118.21 mg/dl (P=0.004) assuming a reduction of 25%. Elevated concentrations of serum cholesterol detected in obese mice were also significantly reduced upon administering the strain of the invention from 176.02 to 143.97 mg/dl (P=0.003) assuming a reduction of 18%. Moreover, the strain of the invention significantly reduces the accumulation of cholesterol and triglycerides in the liver that may contribute to hepatic steatosis.

3.4. Effects of the Administration of the *B. uniformis* CECT 7771 Strain on the Absorption of Dietary Lipids in the Intestine.

Following sacrifice, intestinal tissue samples were taken and washed with saline solution and fixed in 10% buffered formalin, embedded in paraffin, and cut into 4-5 μm sections which were stained with hematoxylin and eosin. The number of chylomicrons or enterocyte fat micelles was determined by counting ten fields in each section fixed with a brightfield microscope (Olympus) and expressed in number of chylomicrons per enterocyte.

Figure 4:
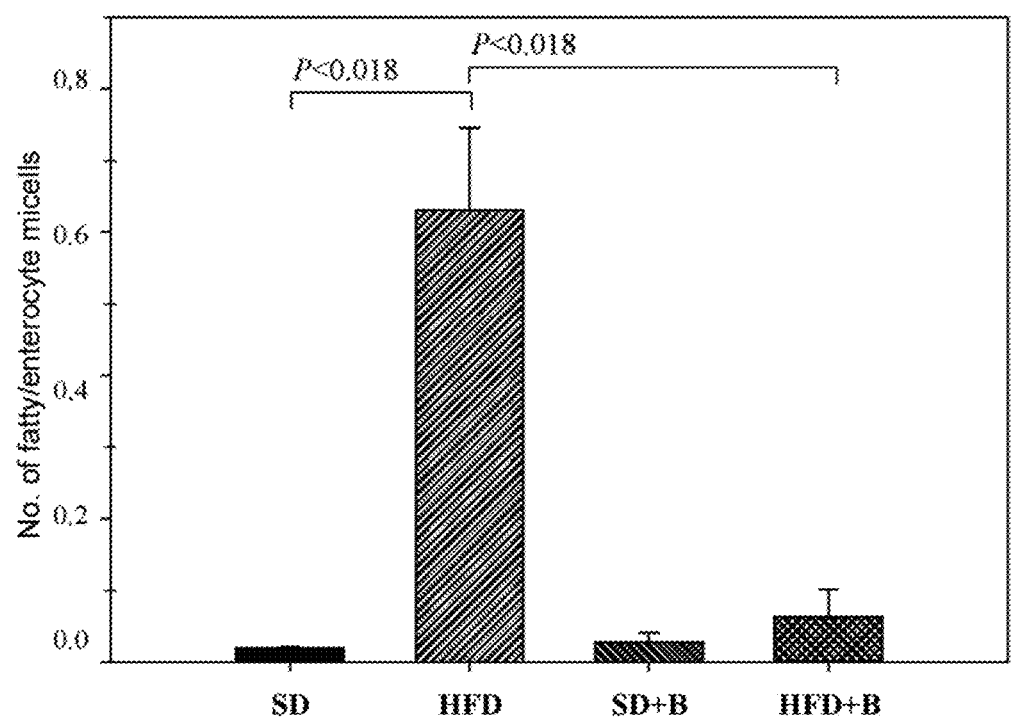
FIG. 4 shows the effect of administering the *B. uniformis* CECT 7771 strain ($5 \times 10^8$ cfu/day) to obese C57BL/6 mice (n=6/group) for 7 weeks on the number of fat micelles accumulated in the enterocytes in histology sections stained with hematoxylin and eosin. SD, control animals with a standard diet, SD+B, control animals with a standard diet+*B.*

As can be seen in FIG. 4, the strain of the invention reduces the number of fat micelles or chylomicra formed in the enterocytes by more than 50%. These results are consistent with those of Table 2, demonstrating that the strain of the invention reduced blood triglyceride levels.

Example 4

Effect of Administering the *B. Uniformis* 7771 CECT Strain on the Function of Immune System Cells; on Immunological Parameters in Peripheral Tissues; and on the Composition of Intestinal Microbiota and its Inflammatory Properties 4.1. Preparation of Cultures of the Strain Object of the Invention.

The *B. uniformis* CECT 7771 strain was grown in Brain Heart broth (Schariab, S. L., Barcelona, Spain) supplemented with 0.05% (w/v) cysteine at 37° C. under anaerobic conditions (AnaeroGen; Oxoid, Basingstoke, UK) for 22 hours. The cells were collected by centrifugation (6,000 g for 15 minutes), washed with a phosphate-buffered saline solution (PBS, 10 mM sodium phosphate, 130 mM sodium chloride, pH 7.4), and re-suspended and administered as a nutritional composition composed of 10% skimmed milk and the bacterial strain at a concentration of 5×10$^8$ cfu of the CECT 7771 strain per 100 μl of composition, similarly to the nutrient composition described in example 3. Aliquots of these suspensions were frozen with liquid nitrogen and stored at −80° C. until use. The viability of the bacteria was tested by counting on Schaedler Agar agar plates (Scharlau, Barcelona, Spain) supplemented with kanamycin (100 mg/L), vancomycin (7.5 mg/L) and vitamin K (0.5 mg/L) after 48 hours of incubation and was approximately 90%. Each aliquot was thawed only once.

4.2. Obesity Animal Model

The same mice were described in example 3 and the same experimental groups were used, two of which were administered the strain object of the invention as a nutritional composition, following the same pattern, and the placebo controls (nutritional composition without the strain). At the end of the treatment period, the animals were anaesthetised and sacrificed by cervical dislocation and various biological samples taken: adipose tissue and pancreas to determine immunological parameters (cytokines), faeces to determine the effect on the composition of the microbiota and immunocompetent cells (macrophages, dendritic cells and T cells) obtained as described below, to evaluate the effect of the intervention on the immune responses of these cells.

4.3. Evaluation of the Effect of Administering the *B. uniformis* CECT 7771 Strain on Macrophage Function in Obese and Normal-Weight Mice.

In order to demonstrate the effect of administering the CECT 7771 strain on improving the response of innate immune system cells, macrophages were aseptically obtained from each experimental group of mice by injecting, via the intraperitoneal route, Dulbecco's Modified Eagles Medium (DMEM) solution (Sigma™—Si Louis, MOAJSA) supplemented with 10% inactivated fetal bovine serum at 56° C. for 30 minutes (Gibco, Barcelona, Spain), 100 μg/ml streptomycin and 100 U/ml penicillin (Sigma Chemical Co.). The macrophages obtained from each group of mice were adjusted to a concentration of $1 \times 10^5$ cells/ml in DMEM and, after incubating for 1 hour at 37° C. in a 5% $CO_2$ atmosphere, the wells were washed with serum-free DMEM to remove non-adherent cells. The adherent cells were incubated for 24 hours and, at the end of this period, were stimulated with 1 μg/ml LPS from *Salmonella enterica* serotype *Typhimurium* (Sigma Chemical Co., Madrid, Spain) to assess their response to a bacterial component of potential pathogens. Additionally, control mice cells were stimulated with faeces (diluted 1/9 in PBS) for each experimental group of mice to determine their inflammatory potential. In parallel, unstimulated macrophages were assessed to determine the basal cytokine production. After stimulation, the supernatants were collected and the concentrations of these cytokines were determined: TNF-α and IL-10 by ELISA (Ready SET Go! Kit, BD Bioscience, San Diego, Calif., USA).

The results obtained indicate that the strain of the invention improves the functioning of innate immune system cells such as macrophages when administered in vivo to normal-weight and obese subjects, increasing their ability to respond to infectious agents, antigens or allergens. In particular, the administration of the strain to animal models of obesity induced by a high-fat diet improves, inter alia, the role of macrophages in phagocytosis and cytokine synthesis (FIG. 5). The administration of the strain increases the respiratory burst of peritoneal macrophages in response to a stimulus or foreign allergen (pathogen), enhancing phagocytic capacity and, therefore, immunological defenses in obese and normal-weight subjects (FIG. 5). This capacity is significantly decreased in obese animals compared to non-obese controls (FIG. 5). Earlier studies also show that the respiratory burst of phagocytic cells responsible for the elimination of pathogens is also altered in subjects with diabetes (Marhoffer et al., 1992. Diabetes Care, 15(2): 256-60). Additionally, the cultivation test with peritoneal macrophages extracted from obese animals and controls and in vitro stimulation thereof with lipopolysaccharide (LPS) of a pathogen, demonstrate that administration of the strain object of the invention improves the synthesis of cytokines responsible for stopping a possible infection such as TNF-α in obese animals (FIG. 5). This macrophage function is also reduced as a result of diet-induced obesity.

4.4. Evaluation of the effect of administering the *B. uniformis* CECT 7771 strain on the function of dendritic cells and T cells of obese and normal-weight control mice.

In order to demonstrate the effect of administering the strain of the invention on the ability of dendritic cells to stimulate T lymphocyte response and thus, the adaptive immune response, the ability of mature dendritic cells to induce the proliferative response of CD4+ T lymphocytes in a mixed lymphocyte reaction. The assay was performed by comparing the responses of dendritic cells extracted from obese and control mice which were administered or not the strain object of the invention as described above.

The dendritic cells were generated from mouse tibia and femoral bone marrow. The tibias and femurs of each mouse were extracted and the surrounding tissue was removed aseptically. After cutting the ends, the bone marrow was extracted by flushing with PBS using a syringe and needle of 0.45 mm in diameter. The obtained cells were washed once with PBS and aliquots of $10^6$ cells diluted in RPMI, supplemented with antibiotics (100 IU/ml penicillin and 100 μg/ml streptomycin), 10% FBS and 20 ng/ml of mouse GM-CSF, and seeded in 100 mm bottles. On the third day, 10 ml of culture medium were added and, on the seventh day, the medium was replaced with fresh medium. On the eighth day, the non-adherent cells were harvested by gentle pipetting. The cells were washed with PBS and re-suspended in culture medium without GM-CSF. The dendritic cells were activated by adding LPS (100 ng/ml) for 24 hours before performing the Mixed Lymphocyte Reaction. Mature dendritic cells were used to stimulate CD4+ T lymphocytes. CD4+ T lymphocytes were isolated from spleens of 7-8 week-old C57BL/6 mice. After being removed, the spleens were suspended in PBS with FBS and passed through a nylon mesh, the cell suspension obtained was washed once and re-suspended in lysis buffer for 5 minutes. After washing twice with PBS, CD4+ T cells were immuno-magnetically separated by positive selection using CD4 (L3T4) Micro-Beads (Miltenyi Biotec GmbH, Bergisch Gladbach, Germany) following the manufacturer's instructions.

In order to perform the Mixed Lymphocyte Reaction, aliquots of dendritic cells were distributed in 96-well plates in triplicate to stimulate, in each case, $1 \times 10^5$ CD4+ T lymphocytes in the following ratios (CD4+ T lymphocytes/dendritic cells): 1:1, 1:2, 1:4 in 100 μl of culture medium and incubated at 37° C. for 72 hours in 5% $CO_2$ atmosphere. Dendritic cells and CD4+ T lymphocytes with and without ConA (5 μg/ml; Sigma), used as mitogen, were used as controls. Lymphocyte proliferation was determined using an ELISA kit (BrdU-colorimetric assay, Roche Diagnostics, Germany) and quantified by measuring absorbance at 440 nm.

In dendritic cell cultures from each experimental group of mice, their ability to synthesise cytokines when stimulated with LPS, as an example of pathogenic stimulation, was also assessed; and in dendritic cell cultures of control mice the potentially inflammatory effect of faeces from each experimental group of mice was determined by measuring cytokine synthesis, as indicated in the case of macrophage cultures. The strain object of the invention has also been shown to enhance the function of dendritic cells and T cells when administered in vivo. Dendritic cells extracted from obese mice that had been administered the strain, incubated in the presence of T cells in various proportions (1:1, 1:2 and 1:4), increase their proliferation and activation ability, properties which are diminished in obese animals which have not been administered the strain (FIG. 6). The improved functioning of the dendritic cells in the obese animals to which the strain was administered is also evident because, after stimulation with LPS in vitro, they are capable of inducing increased secretion of cytokines involved in the response to pathogens (for example TNF-α) (FIG. 6). The administration of the strain object of the patent also increases the capacity of LPS-stimulated dendritic cells to produce the anti-inflammatory cytokine IL10, which helps to regulate inflammation processes, avoiding chronic inflammation. The effects on the described dendritic cells for the strain object of the invention are also significant in normal-weight animals. These properties make the strain object of the patent ideal, as the functionality of dendritic cells and T cells is altered in obesity and related diseases such as diabetes, not always associated with obesity. In particular, dendritic cells exhibit functional alterations associated with weight gain, characterised by their reduced capacity to present antigens and stimulate allogeneic T cells (Macia et al., 2006. J Immunol., 177(9): 5997-6006; Verwaerde et al., 2006. Scand J Immunol., 64(5): 457-66). The pro-inflammatory properties of naïve T cells are increased in response to a stimulus (mitogen or antigen), and can contribute to low-grade chronic inflammatory condition associated with obesity; and, by contrast, T cells previously exposed to antigens present a defect in proliferation and preferably secrete Th2-type cytokines. This explains the high incidence of infections in obese subjects and the lack of response to vaccination and infection mediated by memory T cells (Karlsson et al., 2010. J Immunol, 184: 3127-33). T cell function is also deficient in diabetics, showing reduced capacity to proliferate in response to a stimulus and to synthesise IL2 (Chang y Shaio. 1995. Diabetes Res Clin Pract, 28(2): 137-46).

4.5 Effect of Administering the *B. uniformis* CECT 7771 Strain on Inflammation of Peripheral Tissues.

In order to determine the effect of the strain object of the patent on inflammation in peripheral tissues associated with obesity and related diseases (for example, diabetes), the cytokine concentration in adipose tissue and pancreas was determined after homogenization with a polytron, by ELISA. Obesity increases the concentration of TNF-α and reduces IL-10 in adipose tissue. However, in obese subjects the strain object of the patent reduces the concentration of TNF-α and increases the synthesis of the anti-inflammatory cytokine IL-10 in adipose tissue, reducing inflammation. TNF-α synthesis is increased in obesity and other diseases and contributes to the development of insulin and leptin resistance in tissues, inhibiting its anorectic effects (reducing feelings of hunger) and its role in the regulation of body weight and lipid and glucose metabolism (Example 4, Table 3). Furthermore, in obese subjects, the strain object of the patent reduces the concentration of TNF-α in the pancreas, which can improve the function of this organ in the regulation of glucose metabolism (Example 4, Table 3).

TABLE 3

Cytokine concentration in adipose tissue and pancreas of mice fed a high-fat or standard diet, supplemented or not with the *B. uniformis* CECT 7771 strain.

| | *Experimental groups | | | **Student t test | |
|---|---|---|---|---|---|
| | SD | HFD | HFD + B | Value-P SD vs HFD | Value P HFD vs HFD + B |
| Tissue | Cytokine concentration (Mean ± sd pg/ml) | | | | |
| Adipose | | | | | |
| TNF-α | 1098.1 ± 208.5 | 3075.7 ± 282.8 | 1628.6 ± 407.8 | <0.001 | 0.001 |
| IL-10 | 32089.5 ± 2936.5 | 6578.8 ± 890.3 | 11178.0 ± 1013.5 | <0.001 | 0.005 |
| Pancreas | | | | | |
| TNF-α | 8698.7 ± 822.5 | 10693.6 ± 1481.1 | 2780.3 ± 360.6 | 0.260 | 0.001 |
| IL-10 | 21894.9 ± 1952.3 | 11131.7 ± 2704.3 | 10037.9 ± 759.8 | 0.005 | 0.700 |

*SD: standard-diet group (control) (n = 6); HFD: high-fat diet group (n = 6), HFD + B: HFD group and supplemented orally with $5.0 \times 10^8$ CFU/day of *B uniformis* CECT 7771, for 7 weeks (n = 6). The concentration of cytokines in different tissues was determined by ELISA after sacrifice.
**Significant differences established applying ANOVA and the Student t test for comparisons between two means at a value of P < 0.050.

4.6. Evaluation of the Effect of Administering the *B. uniformis* Strain CECT 7771 Strain on the Composition of the Intestinal Microbiota and Inflammatory Properties.

In order to evaluate the effect of the CECT 7771 strain on the composition of the microbiota, stool samples were collected at the end of the intervention from the different experimental groups of mice, a dilution of 1:10 (w/v) in PBS (pH 7.2) was prepared and, after homogenisation, DNA was extracted using the QIAamp DNA stool Mini kit commercial system (Qiagen, Hilden, Germany). Quantification of the concentration of each bacterial group was performed by real-time PCR using the ABI PRISM 7000-PCR Sequence Detection System (Applied Biosystems, UK). The reaction mixture was composed of 25 SYBR® Green PCR Master Mix (SuperArray Bioscience Corporation, USA), 1 of each primer at a concentration of 0.25 µM and 1 µl of DNA. The concentrations of each bacterial group were determined using the Ct values obtained for each case study. Standard curves were built using plasmid dilutions in which the group-specific PCR-amplified fragment of each bacterial group had been cloned. The results were expressed in number of copies of the 16S rRNA gene per gramme of faeces.

The results show that the *B. uniformis* CECT 7771 strain partially restores the composition of the intestinal microbiota, normalising the alterations associated with excess weight and/or obesity and the inflammatory effect caused by these alterations (FIG. 7), as well as the changes associated with other pathological conditions associated not only to excess weight and/or obesity. The administration of the strain of the invention to a model of obesity increases the number of *Bacteroides* spp. and of the group *C. coccoides* and reduces the number *Bifidobacterium* spp. These changes in the microbiota composition also result in a reduction of the pro-inflammatory properties thereof. Both in macrophages and dendritic cells, the microbiota of obese animals that are administered the strain induces decreased synthesis of pro-inflammatory cytokines, such as TNF-α, with respect to obese animals that are not administered the strain (Example 4, FIG. 7). Alterations in the intestinal microbiota are considered one of the possible inflammatory stimuli that cause weight gain, insulin resistance, obesity and diabetes (Cani y Delzenne 2009. Curr Opin Pharmacol., 9(6): 737-43). Furthermore, these alterations cause other types of pathological conditions. The CECT 7771 strain also induces changes in the microbiota of lean animals, for example, increasing the concentration of *Bifidobacterium* spp. and reducing their ability to induce TNF-α in macrophages and, hence, cause inflammation.

TABLE 4

Example of the effect of administering the CECT 7771 strain on the composition of the intestinal microbiota of obese and normal-weight animals.

| | *Experimental groups | | | | | | |
|---|---|---|---|---|---|---|---|
| | SD | HFD | | SD + B | | HFD + B | |
| Bacterial group | [a]Median (IQR) | [a]Median (IQR) | Valor-p[b] | [a]Median (IQR) | Valor-p[c] | [a]Median (IQR) | Valor-p[d] |
| Total bacteria | 10.8 (10.6-11.1) | 10.5 (10.3-10.8) | 0.092 | 11.4 (11.3-11.6) | 0.010* | 11.0 (10.7-11.2) | 0.629 |
| *Lactobacillus* group | 9.9 (9.4-10.5) | 9.4 (9.2-9.5) | 0.040* | 9.6 (9.3-9.8) | 0.470 | 9.7 (9.5-10.1) | 0.936 |
| *Bacteroides* spp. | 8.4 (8.3-8.6) | 8.7 (8.3-9.0) | 0.674 | 9.3 (9.1-9.5) | 0.004* | 9.0 (8.8-9.3) | 0.016* |
| *Bifidobacterium* spp. | 7.1 (6.8-7.2) | 6.0 (5.9-6.3) | 0.004* | 8.1 (7.9-8.3) | 0.013* | 7.5 (7.0-7.7) | 0.004* |
| *C. leptum* group | 8.4 (8.3-8.6) | 7.6 (7.5-7.7) | 0.004* | 9.6 (9.4-9.8) | 0.004* | 8.5 (8.1-8.7) | 0.936 |
| *C. coccoides* group | 9.1 (8.6-9.3) | 8.4 (8.2-8.5) | 0.016* | 9.9 (9.4-10.0) | 0.054 | 9.6 (9.4-9.7) | 0.036* |
| Enterobacteriaceae | 7.3 (7.2-7.7) | 8.1 (7.8-8.2) | 0.019* | 8.1 (7.6-8.2) | 0.052 | 7.9 (7.5-8.0) | 0.029* |

*SD: standard-diet and placebo group (control) (n = 6);
SD + B: standard-diet group and a daily dose of 5.0 × 10[8] CFU/day of *B. uniformis* CECT 7771 (n = 6);
HFD: high-fat diet and placebo group (n = 6),
HFD + B: high-fat diet group and a daily dose of 5.0 × 10[8] CFU/day of *B. uniformis* CECT 7771 (n = 6). The treatment was maintained for 7 weeks and the placebo or the bacteria were administered daily by gavage.
[a]Results are expressed as the median (interquartile range) of the number of copies of the 16S rRNA gene amplified with group-specific primers specific for each bacterial group per gramme of faeces.
[b]Significant differences between the SD and HFD groups.
[c]Significant differences between the SD and SD + B groups.
[d]Significant differences between the HFD and HFD + B* groups. Significant differences were established at P < 0.050 values, applying the Mann-Whitney U Test.

The invention claimed is:

1. A composition comprising a *Bacteroides uniformis* strain with deposit number CECT 7771 and a carrier and/or excipient.

2. The composition according to claim 1, wherein it further comprises at least an additional microorganism.

3. The composition according to of claim 1, wherein said composition is a pharmaceutical or a nutritional composition.

4. The composition according to claim 3, wherein said nutritional composition is selected from a food, a supplement, a nutraceutical, a probiotic or a symbiotic.

5. The composition according to claim 4, wherein said food is selected from the list consisting of: dairy products, vegetable products, meat products, snacks, chocolate, baby food and drink.

6. The composition according to claim 1, wherein said composition has a strain concentration between $10^3$ and $10^{14}$ colony-forming units (cfu) per gramme or milliliter of final composition.

7. The composition according to claim 1, wherein cells obtained from the strain are in the form of viable or nonviable form.

8. A method for reducing body weight gain or inducing weight loss in a subject for cosmetic purposes that comprises administering the composition according to claim 1, or a nutritional composition according to claim 3 to said subject.

* * * * *